United States Patent
Neri et al.

(10) Patent No.: US 7,232,418 B2
(45) Date of Patent: *Jun. 19, 2007

(54) SUPPORT ELEMENT, AN INTEGRATED MODULE FOR EXTRACORPOREAL BLOOD TREATMENT COMPRISING THE SUPPORT ELEMENT, AN APPARATUS FOR EXTRACORPOREAL BLOOD TREATMENT EQUIPPED WITH THE INTEGRATED MODULE, AND AN ASSEMBLY PROCESS FOR AN INTEGRATED MODULE FOR EXTRACORPOREAL BLOOD TREATMENT

(75) Inventors: Roberto Neri, Mirandola (IT); Roberto Ribolzi, Modena (IT); Jacques Duchamp, Bron (FR); Aziz Aberkane, Decines (FR); Gabriel Meyssonnier, Dizimieu (FR); Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 420 days.

This patent is subject to a terminal disclaimer.

(21) Appl. No.: 10/771,415

(22) Filed: Feb. 5, 2004

(65) Prior Publication Data

US 2004/0162513 A1 Aug. 19, 2004

Related U.S. Application Data

(60) Provisional application No. 60/470,442, filed on May 15, 2003.

(30) Foreign Application Priority Data

Feb. 7, 2003 (IT) .......................... MI2003A0215

(51) Int. Cl.
*A61M 37/00* (2006.01)
*A61M 1/16* (2006.01)
*F04B 43/08* (2006.01)
*B01D 63/00* (2006.01)
*F16K 1/00* (2006.01)
*C02F 1/44* (2006.01)

(52) U.S. Cl. .................... 604/4.01; 604/6.09; 604/6.11; 210/645; 210/321.6; 210/195.2; 417/477.2; 137/861

(58) Field of Classification Search ............... 604/4.01, 604/5.01, 5.04, 6.09, 6.11, 6.16; 210/645–647, 210/90, 525, 232, 195.2; 422/44; 417/477.2, 417/237, 439, 472, 474; 137/861
See application file for complete search history.

(56) References Cited

U.S. PATENT DOCUMENTS

| | | | |
|---|---|---|---|
| 3,909,045 A | 9/1975 | Meagher | 285/22 |
| 4,009,107 A | 2/1977 | Miller et al. | 210/321 B |
| 4,263,808 A | 4/1981 | Bellotti et al. | 73/714 |
| 4,379,452 A | 4/1983 | DeVries | 604/6 |
| 4,424,009 A | 1/1984 | van Os | 417/394 |
| 4,436,620 A | 3/1984 | Bellotti et al. | 210/90 |
| 4,526,515 A | 7/1985 | DeVries | 417/63 |
| 4,637,813 A | 1/1987 | DeVries | 604/6 |
| 4,871,012 A | 10/1989 | Kuo | 165/41 |
| 4,886,431 A | 12/1989 | Soderquist et al. | 417/477 |
| 4,950,245 A | 8/1990 | Brown et al. | 604/153 |
| 5,230,614 A | 7/1993 | Zanger et al. | |
| 5,311,908 A | 5/1994 | Barone et al. | |
| 5,427,509 A | 6/1995 | Chapman et al. | 417/477.2 |
| 5,441,636 A * | 8/1995 | Chevallet et al. | 210/232 |
| 5,462,416 A | 10/1995 | Dennehey et al. | 417/477.2 |
| 5,482,440 A | 1/1996 | Dennehey et al. | 417/63 |
| 5,628,731 A | 5/1997 | Dodge et al. | |
| 5,641,144 A | 6/1997 | Hendrickson et al. | 248/292.13 |
| 5,714,060 A | 2/1998 | Kenley et al. | 210/194 |
| 5,983,947 A | 11/1999 | Utterberg | 138/89 |
| 6,277,277 B1 | 8/2001 | Jacobi et al. | 210/240 |
| 6,308,721 B1 | 10/2001 | Bock et al. | 134/166 R |
| 6,325,775 B1 | 12/2001 | Thom et al. | 604/6.02 |
| 6,630,068 B1 * | 10/2003 | Vinci | 210/240 |
| 6,764,460 B2 * | 7/2004 | Dolecek et al. | 604/6.01 |
| 2005/0049539 A1 * | 3/2005 | O'Hara et al. | 604/4.01 |

| | | |
|---|---|---|
| 2006/0155236 A1* | 7/2006 | Gara et al. ............... 604/4.01 |

FOREIGN PATENT DOCUMENTS

| | | |
|---|---|---|
| AU | 744404 | 1/1999 |
| AU | 199870078 A1 | 1/1999 |
| AU | 199870078 B2 | 1/1999 |
| EP | 0239255 | 9/1987 |
| EP | 0 134 436 B1 | 1/1988 |
| EP | 0362822 | 4/1990 |
| EP | 0 116 596 B1 | 11/1990 |
| EP | 0 282 539 B1 | 1/1992 |
| EP | 0 611 227 A1 | 8/1994 |
| EP | 0 643 808 B1 | 1/1998 |
| EP | 0 695 397 B1 | 9/1998 |
| EP | 0 887 100 A1 | 12/1998 |
| EP | 0 893 603 A2 | 1/1999 |
| EP | 0 694 125 B1 | 2/1999 |
| EP | 0 686 237 B1 | 5/1999 |
| EP | 0 922 256 | 4/2000 |
| EP | 0 992 256 | 4/2000 |
| EP | 1048848 | 11/2000 |
| EP | 0 679 099 B1 | 7/2001 |
| EP | 0 852 953 B1 | 11/2001 |
| GB | 2 076 476 A | 12/1981 |
| GB | 2 110 564 | 6/1983 |
| GB | 2 208 896 A | 4/1989 |
| WO | WO 88/01895 | 3/1988 |
| WO | WO 95/17597 | 6/1995 |
| WO | WO 95/17598 | 6/1995 |
| WO | WO 95/17599 | 6/1995 |
| WO | WO 95/17600 | 6/1995 |
| WO | WO 95/17601 | 6/1995 |
| WO | WO 98/52629 | 11/1998 |
| WO | WO 01/08722 | 2/2001 |

OTHER PUBLICATIONS

International Search Report for International Application No. PCT/IB2004/000104.

* cited by examiner

*Primary Examiner*—Tatyana Zalukaeva
*Assistant Examiner*—Leslie R. Deak
(74) *Attorney, Agent, or Firm*—Finnegan, Henderson, Farabow, Garrett & Dunner, L.L.P.

(57) ABSTRACT

An integrated module for extracorporeal blood treatment has a flat-shaped support element which exhibits on an internal face thereof a complex of fluid distribution lines and on an external face thereof a high-flow dialyzer. The support element has a base body which exhibits fixture seatings, each of which houses an axially extended tract of a fluid distribution line. The tract of the fluid distribution line, with respect to adjacent tracts, has an increased diameter due to the presence of a junction collar made of a rigid material. Each fixture seating exhibits two axial locators for positioning the axially extended tract of a fluid distribution line in a fixed position. The locators interact with the junction collar, and the distribution lines can be fixed to the base body by a resilient fixture of the junction collars in the seatings without gluing. The module is configured to be mounted on an apparatus for intensive treatment of renal insufficiency.

67 Claims, 14 Drawing Sheets

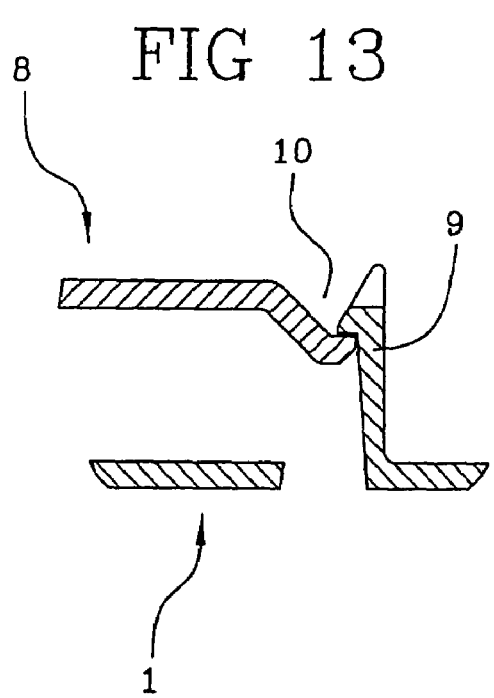
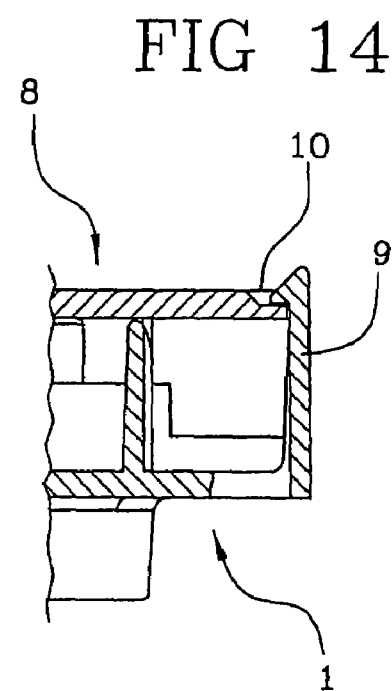
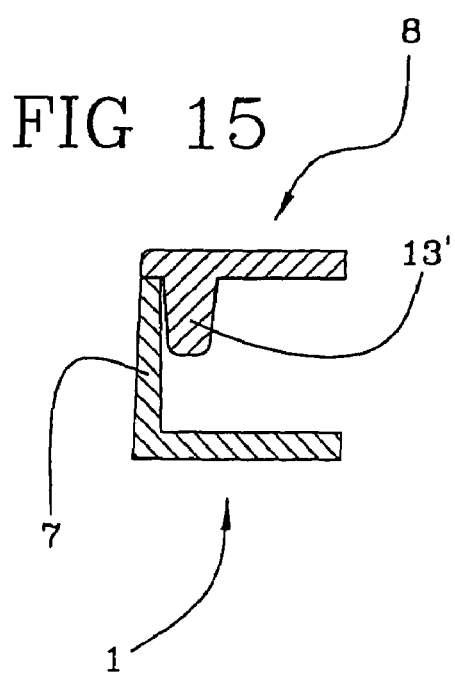
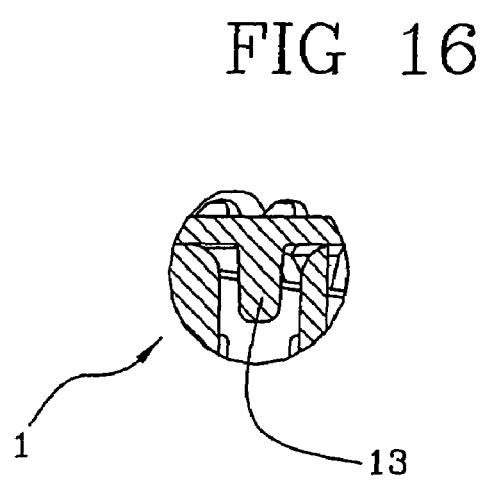

SUPPORT ELEMENT, AN INTEGRATED MODULE FOR EXTRACORPOREAL BLOOD TREATMENT COMPRISING THE SUPPORT ELEMENT, AN APPARATUS FOR EXTRACORPOREAL BLOOD TREATMENT EQUIPPED WITH THE INTEGRATED MODULE, AND AN ASSEMBLY PROCESS FOR AN INTEGRATED MODULE FOR EXTRACORPOREAL BLOOD TREATMENT

CROSS REFERENCE TO RELATED APPLICATIONS

This application claims the priority of Italian Patent Application No. MI2003 A 000215, filed on Feb. 7, 2003, and the benefit of U.S. Provisional Application No. 60/470,442 filed May 15, 2003, the contents of which are incorporated herein by reference.

BACKGROUND OF THE INVENTION

The invention relates to a support element, to an integrated module for extracorporeal treatment of blood comprising the support element, and to an apparatus for extracorporeal treatment of blood equipped with the integrated module. The invention further relates to an assembly process of an integrated module for extracorporeal treatment of blood.

Specifically, though not exclusively, the invention can be usefully applied to the field of extracorporeal treatment of blood for treatment of renal insufficiency.

The prior art teaches apparatus for blood treatment which remove blood from the patient in a line, carry out an extracorporeal treatment on the blood and then return the treated blood to the patient. Apparatus of this type are used for various treatments; for example therapeutic and non-therapeutic plasmapheresis, extracorporeal oxygenation of blood, purification of blood and removal of water in cases of renal insufficiency. The present invention will be described with particular reference to intensive treatment of renal insufficiency, without any limitation being placed on the ambit of the invention to this specific application thereof.

EP 0 611 227 teaches a multifunctional integrated module for application to a multifunction apparatus for intensive treatment of renal insufficiency, in particular for hemodialysis, hemofiltration and hemodiafiltration. The integrated module comprises a support element, a blood treatment device mounted on the support element and a complex of fluid distribution lines cooperating with the treatment device and associated to the support element. The blood treatment device comprises a semi-permeable membrane which separates two chambers. The distribution line complex comprises a blood withdrawal line from the patient (or arterial line) connected to an inlet of a first chamber of the treatment device, a return line (or venous line) of the treated blood to the patient, connected to an outlet of the first chamber, an infeed line of a treatment fluid (for example a dialysis liquid) connected to an inlet of the second chamber of the treatment device, a waste fluid discharge line connected to an outlet of the second chamber, an infusion line of a substitution liquid which is introduced into at least one of the blood lines, an anticoagulant infusion line which is introduced into the arterial line. The support element comprises a plate-shaped body made of press-formed plastic material. The complex of fluid distribution lines is fixed to the support element at gluing points and zones which are predefined on an internal face of the plate-shaped body, while the treatment device is mounted on the external face of the plate-shaped body itself.

During use, the integrated module is mounted on the blood treatment device and set up following a predefined and simple interconnection procedure so that the treatment device is connected, by the distribution lines, to the cardiovascular system of the patient as well as to suitable containers for access and collection to and of the fluids used in the process. Some distribution lines of the module are coupled with respective peristaltic pumps which the apparatus is equipped with. The pumps invoke circulation of the fluids in the lines; the lines are each provided with a U-shaped arched segment, preformed during assembly of the module and intended for coupling to a pump. On mounting the integrated module on the apparatus the various arched segments of the distribution lines are easily couplable about the peristaltic pumps, so that the latter are immediately operative.

The integrated module is of a disposable type, i.e. destined to be disposed of, usually after a first use, and substituted by another.

The above-described integrated module has the advantage of being easily and rapidly installed on the treatment device. The simple and rapid set-up of the module is particularly advantageous for renal insufficiency intensive treatments, in which the personnel at work is often not expert in the use of machines for blood treatment and where the urgent readying and application of the machine is often of vital importance. Similarly, the dismounting of the module is equally rapid and simple.

The prior art as described above is susceptible to improvement at various levels:

firstly, the fact that the integrated module has to be totally eliminated after use, including parts such as, for example, the plastic support element, which does not come into direct contact with bodily fluids;

secondly, the assembly of the integrated module, which is a rather delicate stage, as high precision of positioning of the U-segments of the distribution lines on the support element is required, so that correct coupling with the peristaltic pumps can be achieved;

thirdly, in relation to the long set-up times and high costs of assembly of the integrated module, which must include a relatively complicated and laborious stage of precise positioning and gluing of the various distribution lines in predetermined gluing zones on the support element.

SUMMARY OF THE INVENTION

The present invention provides a support element for an integrated module for extracorporeal blood treatment thanks to which the module itself can be rapidly assembled and mounted on a blood treatment device.

The invention enables a simplification of the operations for assembly of the integrated module, reduces the scope for error in positioning the distribution lines on the support element, improves precision in the couplings between the U-segments of the distribution lines and the peristaltic pumps of the blood treatment apparatus, enables, after use, a simple and practical separation of the support element from the fluid distribution lines, reduces assembly costs and times of the integrated module.

The above objectives are all achieved by a support element made according to one or more of the appended claims.

BRIEF DESCRIPTION OF THE DRAWINGS

Further characteristics and advantages of the invention will better emerge from the detailed description of a preferred but non-exclusive embodiment of a support element according to the present invention. The description is made herein below with reference to the accompanying figures of the drawings, which are given by way of example and which are non-limiting.

FIGS. from 13 to 16 show, in section, four coupling zones between the cover and the base body.

Figure 17:
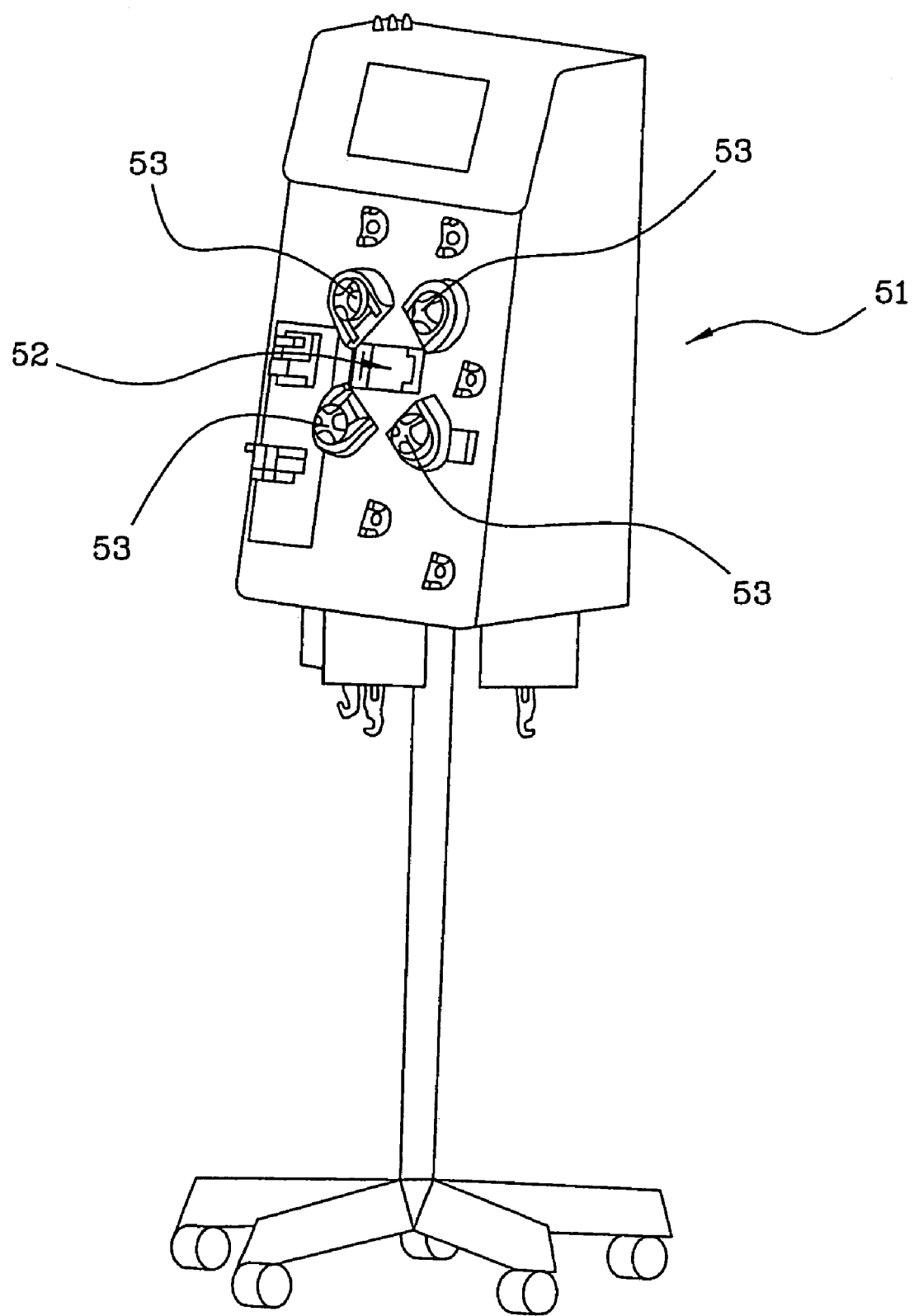

FIG. 17 is an apparatus for intensive treatment of renal insufficiency predisposed to receive an integrated module for blood treatment comprising the support element of the preceding figures.

Figure 18:
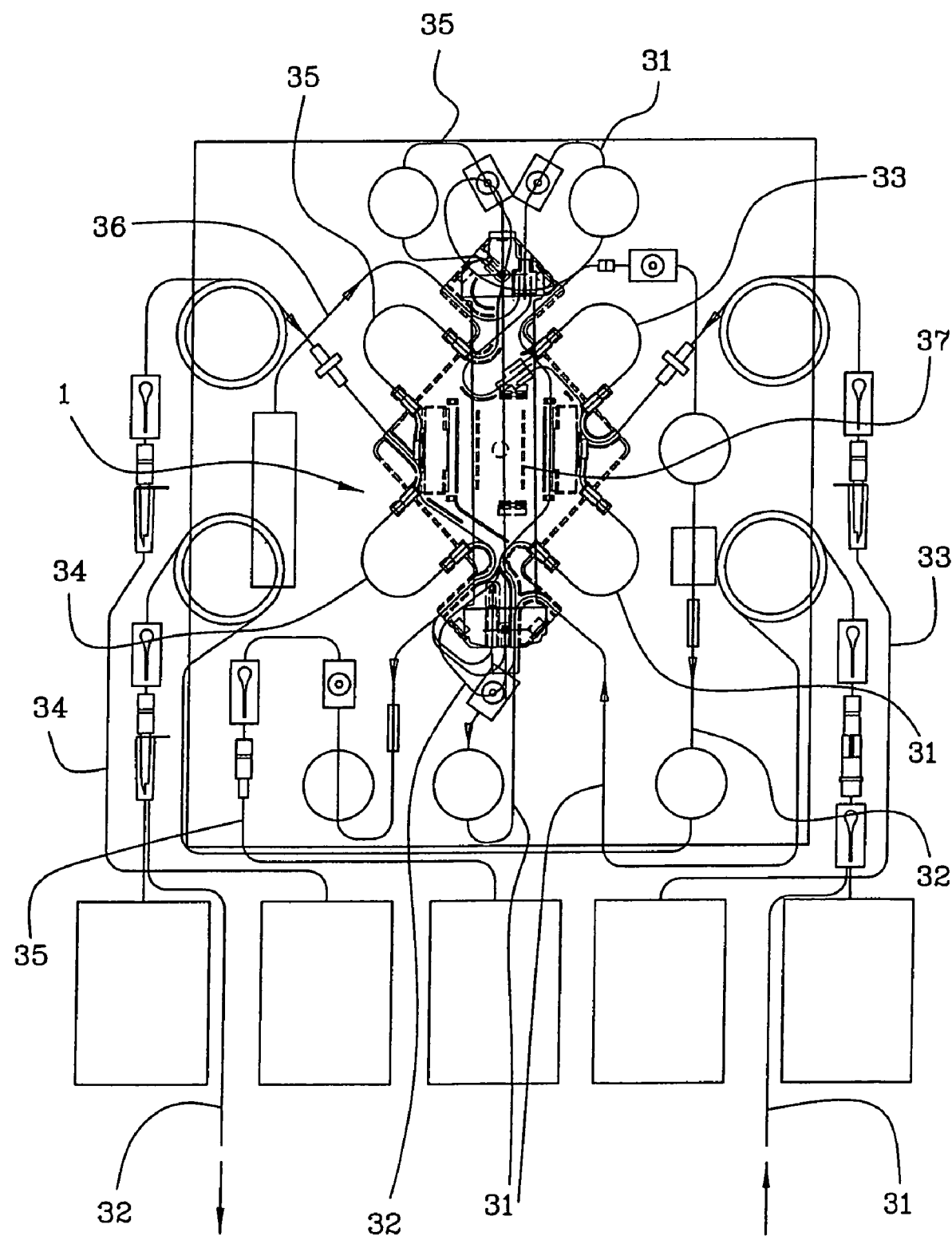

FIG. 18 is a diagram of a multifunctional integrated module, able to perform treatments with a pre-infusion of liquid into the extracorporeal blood circuit, operatively connected to the apparatus of FIG. 17.

Figure 19:
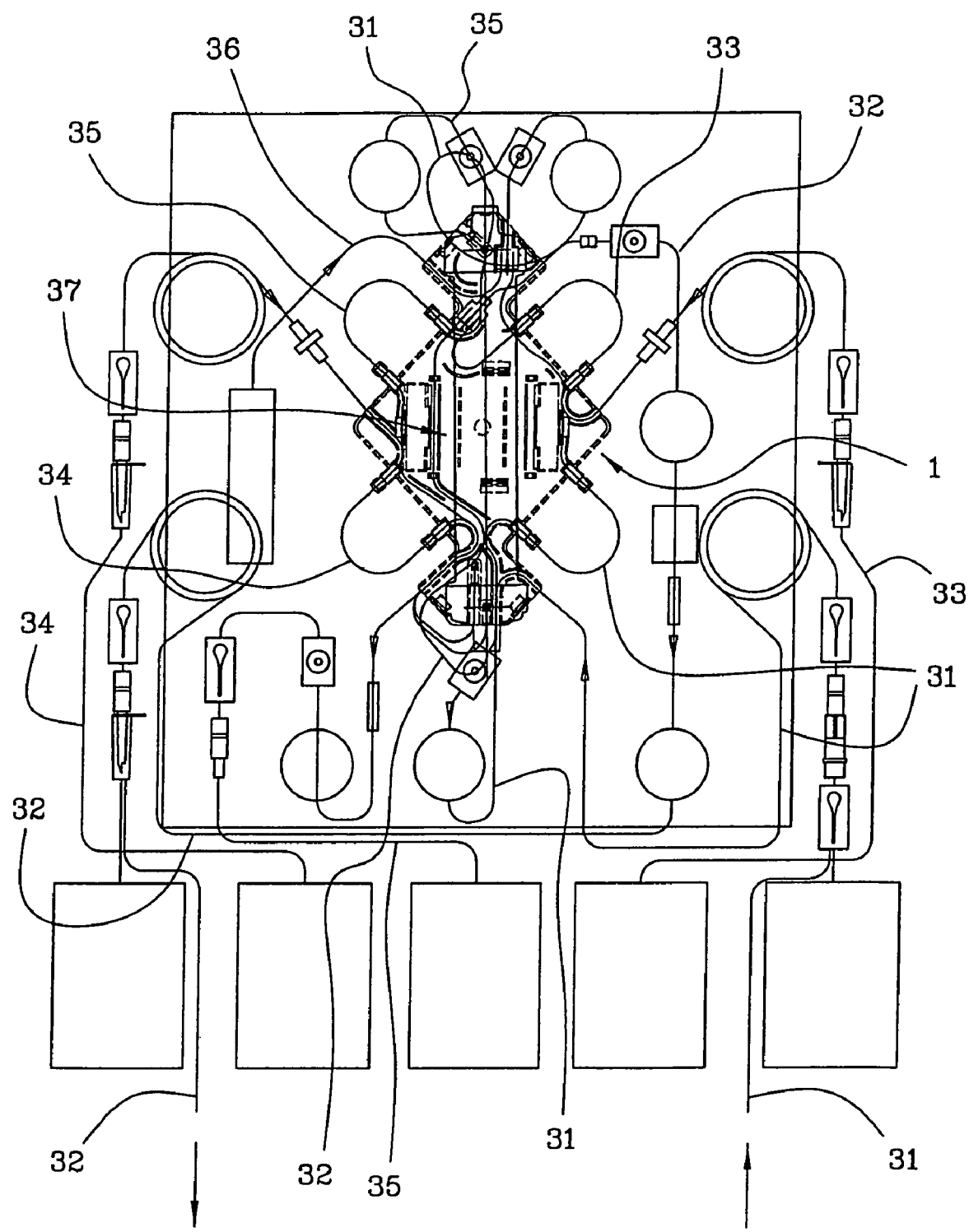

FIG. 19 is a diagram of another multifunctional integrated module, able to perform a post-infusion, associated to the apparatus of FIG. 17.

Figures 20, 21, 22:
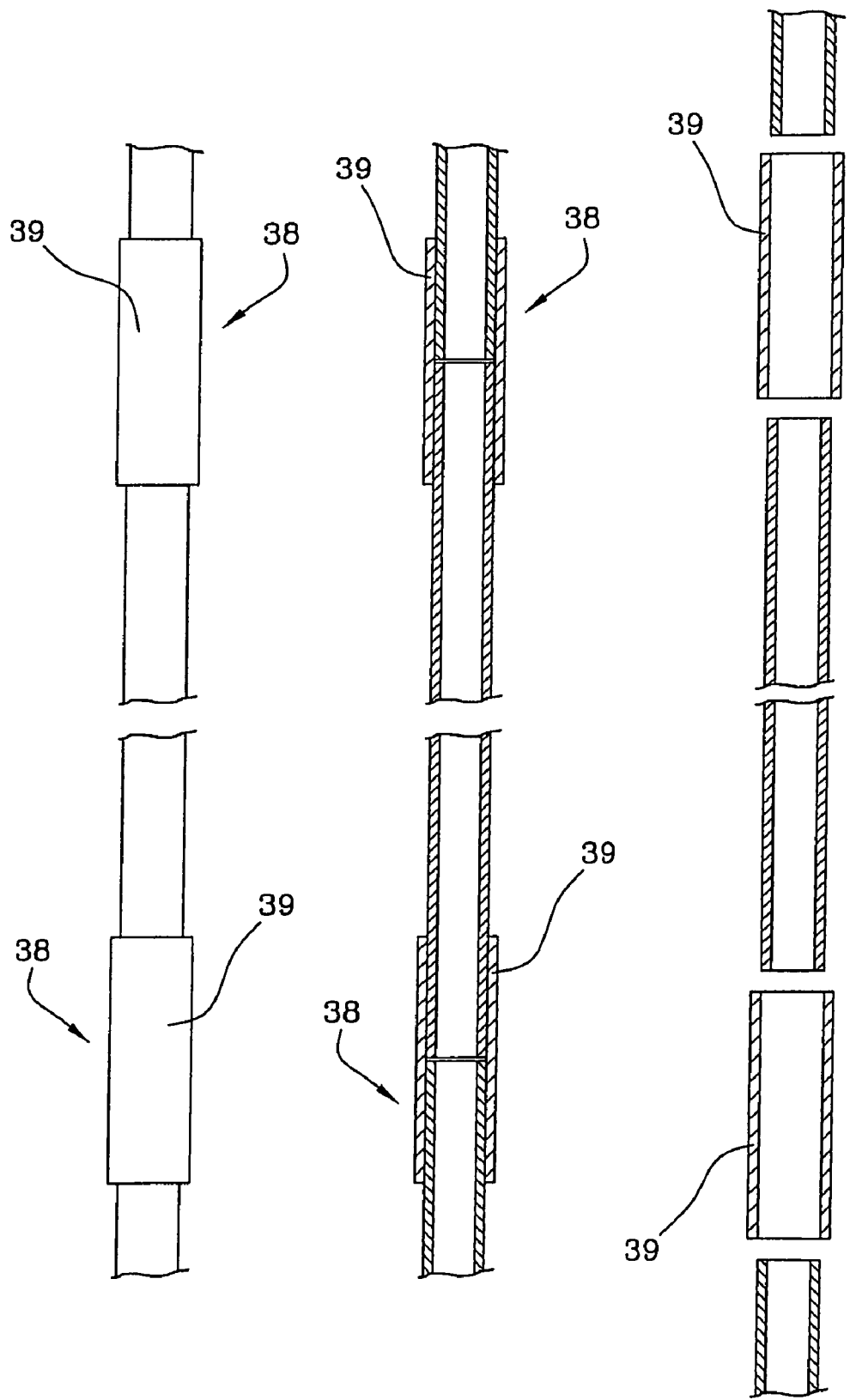
Figure 23:
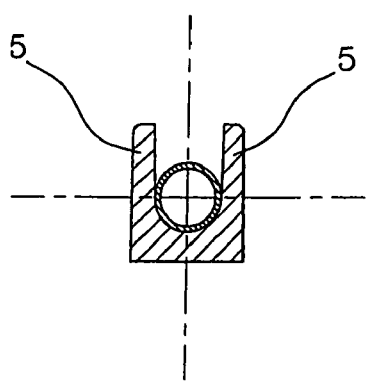
Figure 24:
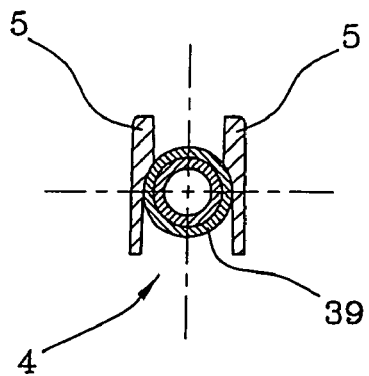
Figure 26:
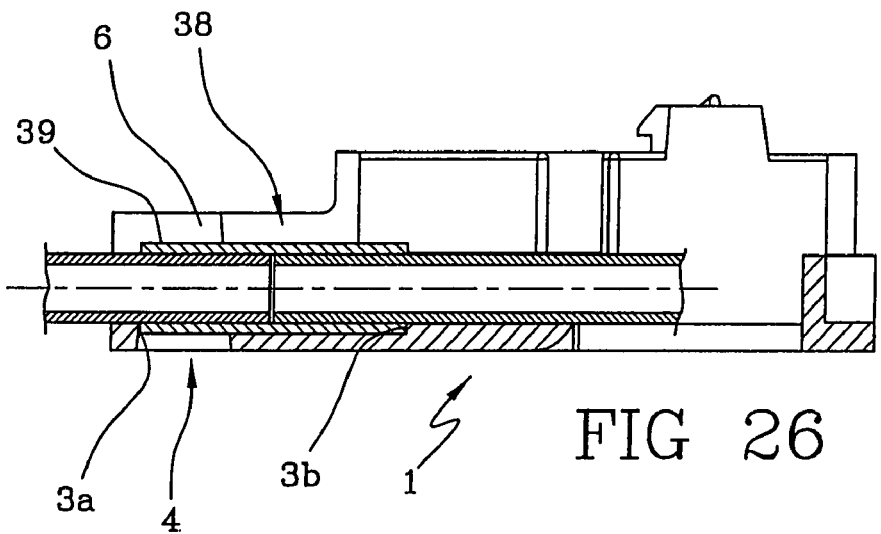
Figure 25:
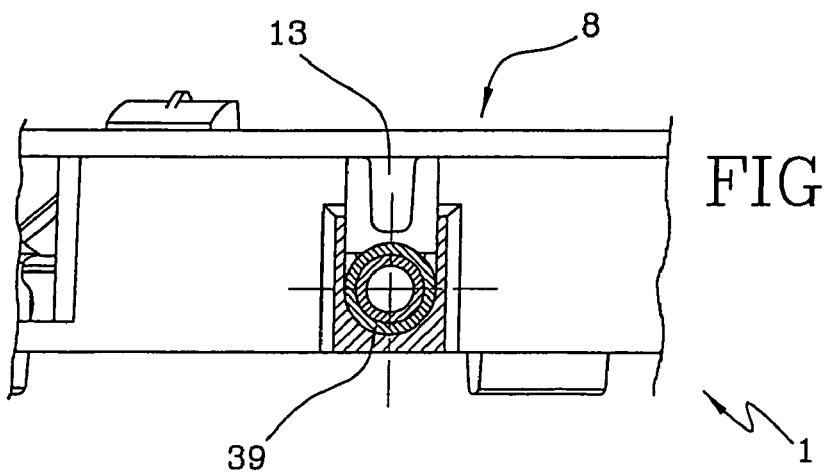

FIG. 20 is a tract of a distribution line including a pump segment comprised between two joint collars 39.

FIG. 21 is a longitudinal section of FIG. 20.

FIG. 22 is an exploded view of FIG. 21 in which some components of the distribution line are illustrated before assembly.

FIGS. 23, 24, 25 and 26 show FIGS. 5, 6, 7 and 9 with the joint collar 39 coupled in the fixture seating.

LEGEND

1 Base body of the integrated module for extracorporeal blood treatment
2 Fixture seatings for joint-fixture of line tracts 38
3a Axial reference locator for positioning of a line tract 38 arranged in the fixture seating 2 in an external direction of the base body 1
3b Axial reference locator cooperating with locator 3a and arranged in the fixture seating in an internal direction of the base body 1
4 Through-hole located on the bottom of the seating 2 through which an extraction force can be applied from below on the tract of line 38 constrained in the fixture seating 2
5 Lateral walls laterally defining the fixture seating 2
6 Reliefs developing in an internal direction of the fixture seating 2 from the lateral walls 5
7 Raised edge rising from the perimeter of the base body 1
8 Cover of the integrated module couplable to the base body 1
9 Flexible tabs associated to the base body 1 for fitting the cover 8
10 Recesses on the cover 8 cooperating with the tabs 9
11 Guide channels associated to the base body 1 for housing two superposed channels of the fluid distribution line
12 Joint elements associated to the base body 1 for receiving and constraining the fluid distribution lines
13 Teeth projecting downwards from the cover 8 for limiting the raising of the tracts of line 38 constrained in the fixture seatings 2
13' Teeth projecting downwards from the cover 8 and situated in proximity or in contact with the internal side of the raised edge 7 for aiding fitting and positioning of the cover 8 on the base body 1
14 First connector associated to the base body 1 for mounting the treatment device 37 to the base body 1
15 Second connector for mounting the treatment device 37
16 Third connector for mounting the treatment device 37
17 First terminal portion of a connector for fluid connection with the treatment device 37
18 Second terminal portion of a connector for fluid connection with a fluid distribution line
19 Sealing collar external of the first terminal portion 17
20 Connection wall connecting the sealing collar 19 with the first portion 17
31 Blood withdrawal line (arterial line)
32 Blood return line (venous line)
33 Substitution fluid infeed line (pre-infusion line and/or post-infusion line according to the type of integrated module)
34 Supply line of a treatment fluid (for example, a dialysis liquid)
35 Discharge line of a waste fluid
36 Supply line of an anticoagulant fluid
37 Blood treatment device (for example a dialysis filter)
38 Axial tracts of line with increased external diameter, destined for use in the fixture seatings 2 on the base body 1
39 Joint collars causing the increase in diameter of line tracts 38
51 Apparatus for extracorporeal blood treatment destined to receive the integrated module
52 Housing zone for the integrated module on the apparatus 51
53 Peristaltic pumps predisposed on the apparatus 51.

DETAILED DESCRIPTION

The support element is used as a component of a multifunctional integrated module for extracorporeal blood treatment, in which the integrated module is operatively associable to a multifunctional apparatus for treatment of renal insufficiency. The integrated module is used in particular for intensive treatment of renal insufficiency.

The integrated module comprises the support element, a blood treatment device mounted on the support element, and a complex of fluid distribution lines associated to the support element and cooperating with the treatment device. Each distribution line comprises at least one flexible tube.

The Support Element.

With reference to FIGS. from 1 to 16, the following is a description of the support element. It comprises a base body 1 which in turn comprises a part consisting of a flat plate with a plurality of perimeter edges giving the body 1 a polygonal shape. In more detail, the flat plate has a rhomboid central part and two projecting parts, upper and lower, also rhomboid and extending along a common longitudinal axis.

The base body 1 exhibits means for connecting, for receiving and constraining the complex of fluid distribution lines. The means for connecting project from an internal face of the flat plate of the base body 1 and are made in a single piece there-with by press-forming (injection) of a plastic material.

The means for connecting the complex of lines comprise a plurality of fixture seatings 2 located on the periphery of the central rhomboid part of the base body 1. In more detail, the base body 1 exhibits two fixture seatings 2, paired and beside the other, for each side of the rhombus. Each fixture seating 2 is predisposed and configured for a resilient press-fitting and joint-fitting of a corresponding tract of a fluid distribution line, as will better emerge from the following description.

Each fixture seating 2 is axially elongate, in the shape of a superiorly-open channel, for receiving a corresponding axially elongate tract of a fluid distribution line. The housing channel is also open at opposite ends thereof. Each fixture seating 2 is provided with two axial reference locators 3a, 3b, respectively external and internal, axially distanced and opposite, between which the tract of line will be positioned and constrained. Each fixture seating 2 can be provided with a single reference locator 3a or 3b for the positioning of the tract of line in the fixed position.

Each axial locator 3a, 3b, is fashioned from a raised edge projecting towards the inside of the fixture seating 2 at an axial end opening of the fixture seating 2. The raised edge cooperates contactingly with a corresponding projection, in the form of an annular abutment, predisposed externally of the tract of line destined to be engaged in the fixture seating 2, as will be better explained herein below. The coupling between a projection on the tract of line and the corresponding internal raised edge determines a correct and precise positioning of the tract of line in the fixture seating 2.

In more detail, the means for connecting the lines comprise a plurality of pairs of fixture seatings 2; the fixture seatings of each pair are situated side-by-side on the periphery of the base body 1 and receive and constrain two tracts of end of a U-shaped arched segment of a line. Each pair of fixture seatings 2 is arranged on a different perimeter side of the rhomboid central part of the base body 1, each pair having a different orientation with respect to the other pairs. The U-shaped segment cooperates with a peristaltic pump belonging to the treatment apparatus, as will be better explained herein below (the segment is known as the pump segment for this reason). The U-shaped pump segment projects externalwise beyond the periphery of the base body 1.

In more detail, each fixture seating 2 extends axially in length, with a rounded-U-shaped transversal section, to receive an axial tract of a fluid distribution line, and exhibits at two opposite axial ends two undercut surfaces corresponding to two opposite axial directions of the tract of fluid distribution line in the longitudinal seating. The two axial undercut surfaces are fashioned from the two above-mentioned raised edges and result in axial locators 3a and 3b which, as mentioned above, determine the axial positioning of the tract of line in the constrained position thereof.

The upper opening for forced insertion of the tract of line has at least one end part, facing externalwise of the base body 1 (i.e. towards the U-shaped arched segment of the corresponding fluid distribution line), having a passage section which is narrower than the maximum width of the seating: that is, the upper entrance to the channel is narrower with respect to the "real" width of the seating, i.e. the part of the seating where the tract of line is housed when in the constrained position. The tract of line inserted into the channel of the seating has an external diameter which is greater than the minimum width of the passage section, so as to create a friction insertion, and has a diameter which is about equal to the maximum width of the fixture seating, so that the tract of line inserted and fixed in the seating is not crushed, or in any case only very lightly crushed by the walls of the seating.

Each fixture seating 2 inferiorly exhibits a through-hole 4, facing the upper insertion opening, through which a pressure from below can be exerted on the tract of line constrained in the fixture seating in order to extract it (if this is envisaged after use of the integrated module) through the upper insertion opening.

Each fixture seating 2 exhibits an axial end tract which extends axially internally of the perimeter of the base body 1 and an axial end tract which extends externally.

As mentioned above, each fixture seating 2 comprises an upper opening for insertion of a tract of line predisposed for the insertion. At least a part of the length of the upper opening projects externally beyond the perimeter edge of the base body 1. In more detail, the opening is laterally delimited by two lateral walls 5 located side-by-side, each of which walls 5 exhibits an upper edge. The upper opening of the channel is delimited by the upper edges of the two lateral walls 5. In the part of the opening projecting beyond the base body 1, the two upper edges of the lateral walls 5 are straight (and continuous) and parallel one to another, so that the upper opening of the seating extends in a same plane as the lie plane of the upper edges of the lateral walls 5, which are conformed so that the upper opening is flat and extends throughout the length of the seating, or at least for the part thereof which extends beyond the perimeter edge of the base body 1.

Each of the two lateral walls 5 internally exhibits a lateral relief 6 projecting from the wall 5 towards the inside of the opening to define an undercut surface with respect to an extraction direction of the tract of line through the upper opening of the seating: the two reliefs 6, one for each lateral wall 5, face towards and cooperate with each other in order to obstruct the extraction of the tract of line from the channel of the seating.

Each undercut surface, and the lateral relief 6 giving rise to the undercut surface, is predisposed inferiorly of the upper edge of the lateral wall 5; in other words each lateral relief 6 emerges laterally from a side of the lateral wall 5, without emerging upwards, i.e. beyond the upper edge of the wall 5 itself. Each lateral relief 6 is situated in a part of end of the seating facing towards the U-shaped line segment (the pump segment). Each undercut surface is inclined with respect to the extraction direction of the tract of line so that the line can be extracted by force; in effect, the undercut surface lends a certain stability to the positioning of the tract of line with respect to extraction, while the inclination of the undercut surface is such that, by acting with an appropriate extracting force, the tract of line can be removed from its fixture seating.

Each fixture seating 2 exhibits two series of undercut surfaces which operate in two reciprocally transversal directions of movement of the tract of line with respect to the seating: one of the directions is that of axial sliding (in this case the undercut surfaces are situated on the locators 3a and 3b and act in opposite directions) and the other direction is the extraction direction, through the upper opening for forced insertion. The combined action of these undercut surfaces determines the stable and precise positioning of the tract of line in the fixture seating 2.

The internal face of the base body 1, i.e. the face from which the means for connecting for the various lines emerge, exhibits a raised perimeter edge 7 for laterally containing at least a part of the complex of distribution lines.

In other words, the base body 1 comprises a vertical front wall (where front and vertical relate to the work position of the module on the blood treatment apparatus) which comprises the flat plate-shaped part, and a perimeter wall (i.e. the raised edge 7) arranged on the back of the front wall (once more with reference to the work position of the integrated module when mounted on the apparatus). The perimeter wall in effect develops in a distancing direction from the posterior side of the front wall and defines a work seating in which at least a part of the complex of fluid distribution lines can be housed, which lines are destined to be associated to the support element. The height of the raised edge 7 is at least double that of the external diameter of a tube of a fluid distribution line; therefore the work seating can contain two tubes, one above another.

The support element further comprises a cover 8 coupled to the base body 1, which cover 8 is provided for closing at least a part of the complex of distribution lines associated to the means for connecting. The cover 8 at least partially closes the work seating housing the lines. The cover 8 helps keep the fluid distribution lines in a stable position in the work seating. The cover 8, with the module in the work position on the apparatus, is situated behind the front wall of the base body 1.

The base body 1 comprises means for hooking for removably coupling the cover 8 to the base body 1, made in a single piece with the base body 1 itself. A part of the means for hooking is predisposed on the perimeter of the base body 1, while another part thereof is arranged internally of the perimeter. The means for hooking comprise a plurality of flexible tabs 9 which emerge from the base body 1 and which are each provided with an engaging tooth which couples with a recess 10 in the cover 8. The cover 8 exhibits at its centre a through-hole on a rim of which some of the recesses 10 are afforded, while others of the recesses 10 are arranged on the external perimeter.

Various guide channels of the distribution lines emerge from the internal face of the base body 1; these channels are both curved and straight and define pathways followed by the distribution lines. Each channel is defined by two lateral walls, side-by-side and parallel. The reciprocal distance of two side-by-side walls is about equal to an external diameter of the tubes. For some channels, indicated by 11, the lateral walls are configured and arranged in such a way that a height of the channel is at least double a width thereof; these channels 11 are able to house or laterally contain two tracts of line, one above another.

The internal face of the base body 1 also exhibits some pairs of fixture elements 12 for resilient fixture of lines. The fixture elements 12 of each pair cooperate and are arranged one in front of another in a same pair; they hold the distribution lines firm and tight.

The cover 8 closes off at least a part of the internal face bearing the means for connecting the lines. The cover 8 extends in a sort of flat plate shape, with a perimeter that corresponds to the perimeter of the internal face of the base body 1. Thus it comprises a rhomboid central part with two end parts, one upper and the other lower, also rhomboid and arranged along a median longitudinal axis of the cover 8. At a centre thereof the central part of the cover 8 exhibits the above-cited through-hole, which is rectangular in shape. With the cover 8 coupled to the base body 1, a containment space is defined between the internal face of the base body 1 and an internal face of the cover 8, which closes at least a part of the complex of distribution lines.

On a periphery of the central part thereof, the cover 8 exhibits a plurality of teeth 13, projecting downwards, each of which is associated to a fixture seating 2. Each tooth 13, when the cover 8 is coupled to the base body 1, at least partially enters a respective fixture seating and thus limits a raising of the tract of line constrained in the fixture seating 2. When the cover 8 is mounted on the base body 1, the lower end of each tooth 13 is located slightly above the undercut surface on the relief 6 which prevents a raising of the tract of line constrained in the fixture seating 2. Should the tract of line be raised beyond the undercut surface, the teeth 13 provide a guarantee against further raising thereof.

On an external face thereof located opposite to the internal face, the base body 1 also exhibits means for connecting, for attaching a blood treatment device (for example a high-flow dialyzer). The means for connecting are also made in a single piece with the base body 1, by press-forming. The means for connecting the dialyzer comprise a first and a second connector, 14 and 15, associated to the base body 1 and located at a distance one from the other; they are destined to receive and engage with corresponding seatings afforded on the blood treatment device which is mountable on the support element. The first and second connectors 14 and 15 are made in a single piece with the base body 1. There is also a third connector 16, distanced from the first and second connectors 14 and 15 and made in a single piece with the base body 1. The three connectors 14, 15 and 16 define, in combination one with another one, a plurality of pairs of connectors having differentiated interaxes for engaging with corresponding pairs of seatings associated to different blood treatment devices mountable on the support element. The three connectors 14, 15 and 16, are unaligned with one another.

Each connector 14, 15 and 16 defines a fluid passage having a first terminal portion 17, destined to be set in fluid communication with a corresponding channel in a respective seating on the blood treatment device, and a second terminal portion 18, destined to be set in fluid communication with one of the fluid distribution lines associable to the base body 1. The fluid passage is integrated in the connectors 14, 15 and 16, which are in turn made in a single piece with the base body 1.

In more detail, each connector 14, 15, 16 comprises a tubular channel, which defines the first terminal portion 17, a sealing collar 19, located in a radially external position to the tubular channel, and a connecting wall 20 which develops continuously between an external lateral surface of the tubular channel and an internal lateral surface of the sealing collar 19, defining an annular seating for engaging each seating. The tubular channel is coaxially arranged with respect to the sealing collar 19. The annular seating exhibits a bottom which is delimited by the connecting wall 20. The annular seating exhibits an increasing radial dimension as it progresses from the bottom connecting wall 18; it comprises a first zone, adjacent to the bottom and having a constant radial dimension; a second zone, distal with respect to the bottom and having a constant radial dimension which is greater than the radial dimension of the first zone; and a third zone, which is a transit zone between the first and second zones and which has a progressively growing radial dimension as it progresses away from the bottom connecting wall 20.

Each connector 14, 15 and 16, is directly constrained to the base body 1.

The tubular channel, i.e. the channel defining the first terminal portion 17, and the sealing collar 19 of each seating 14, 15 and 16, are parallel to one another in the base body 1, defining a single coupling direction with the corresponding connectors of a treatment device.

The base body 1 and the connectors 14, 15 and 16 of the blood treatment device (located on the external face of the base body 1) are made of a rigid material in order to offer a good mechanical support for the device.

The Complex of Fluid Distribution Lines.

The fluid distribution lines comprise flexible tubes having internal sections for fluid passage which internal sections are the same for all the tubes.

The complex of fluid distribution lines associated to the support element comprises: a blood withdrawal line 31, a blood return line 32, a substitute fluid infeed line 33, a treatment fluid infeed line 34 (for example a dialysis liquid), a waste fluid discharge line 35, and an anticoagulant infeed line 36.

37 denotes a blood treatment device mounted on the support element and comprising a first and a second chamber, separated from each other by a semi-permeable membrane. The blood treatment device 37 is selected from a group comprising devices for: hemofiltration, hemodialysis, high-flow dialyzers and hemodiafiltration devices. In the illustrated embodiment the treatment device is a high-flow dialyzer.

The blood withdrawal line 31 is connected to the first chamber of the treatment device 37. The blood return line 32 receives the treated blood exiting from the first chamber and returns it to the patient. The treatment fluid infeed line 34 is fluidly connected to an inlet of the second chamber of the blood treatment device 37. The treatment fluid (dialysis liquid) is destined to receive, through the semi-permeable membrane, the impurities present in the patient's blood and the excess fluid which is to be removed from the blood. The waste fluid discharge line 35 is fluidly connected to an outlet of the second chamber and carries the waste fluid exiting from the blood treatment device 37 to a collection recipient.

The blood treatment device 37 comprises a blood withdrawal port, a blood return port, a treatment fluid inlet port and a waste fluid discharge port, in fluid connection (respectively) with the blood withdrawal line 31, the blood return line 32, the treatment fluid supply line 34 and the waste fluid discharge line 35.

Figure 1:
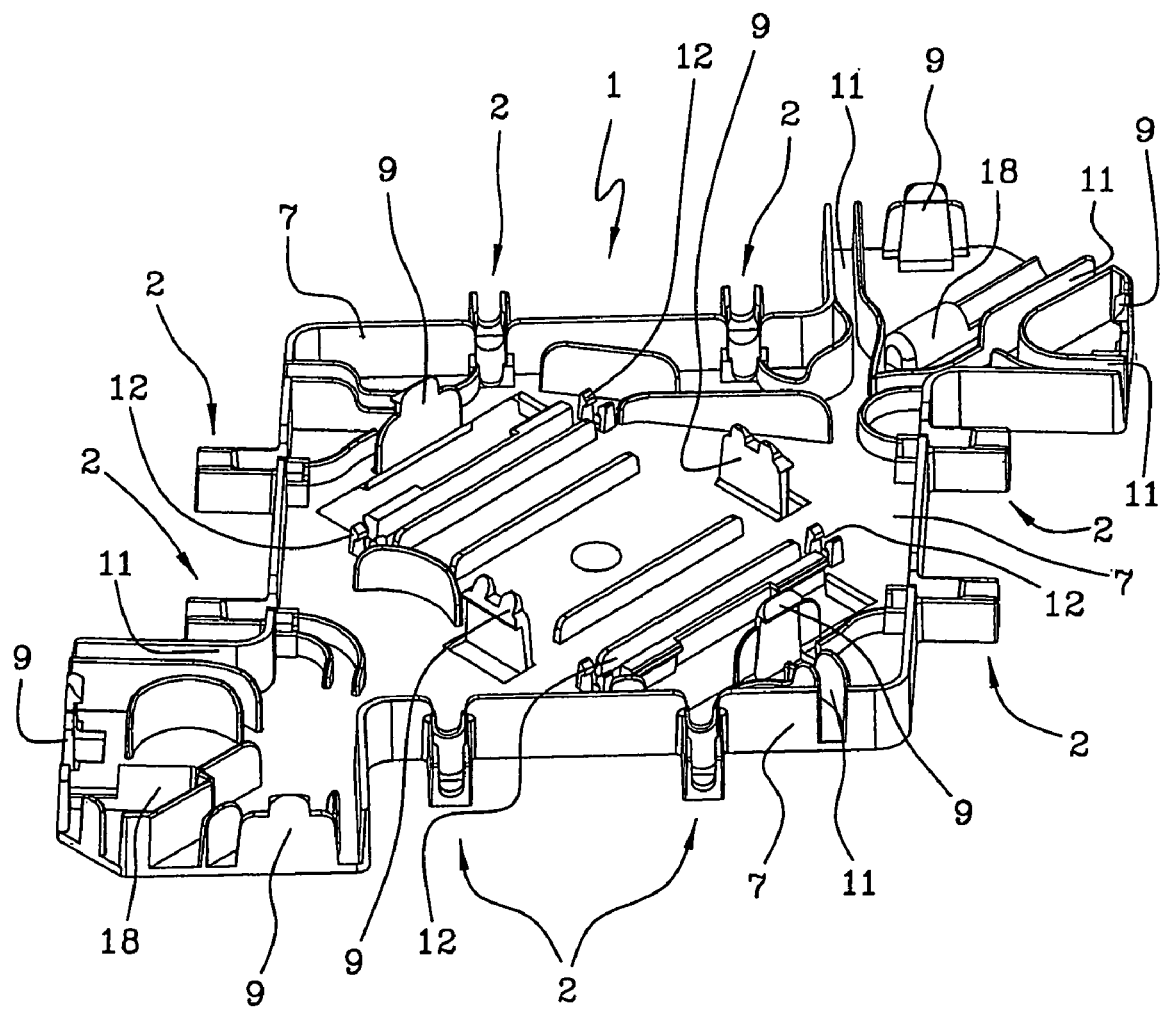
FIG. 1 is a perspective view of the internal face of the base body of the support element.
Figure 2:
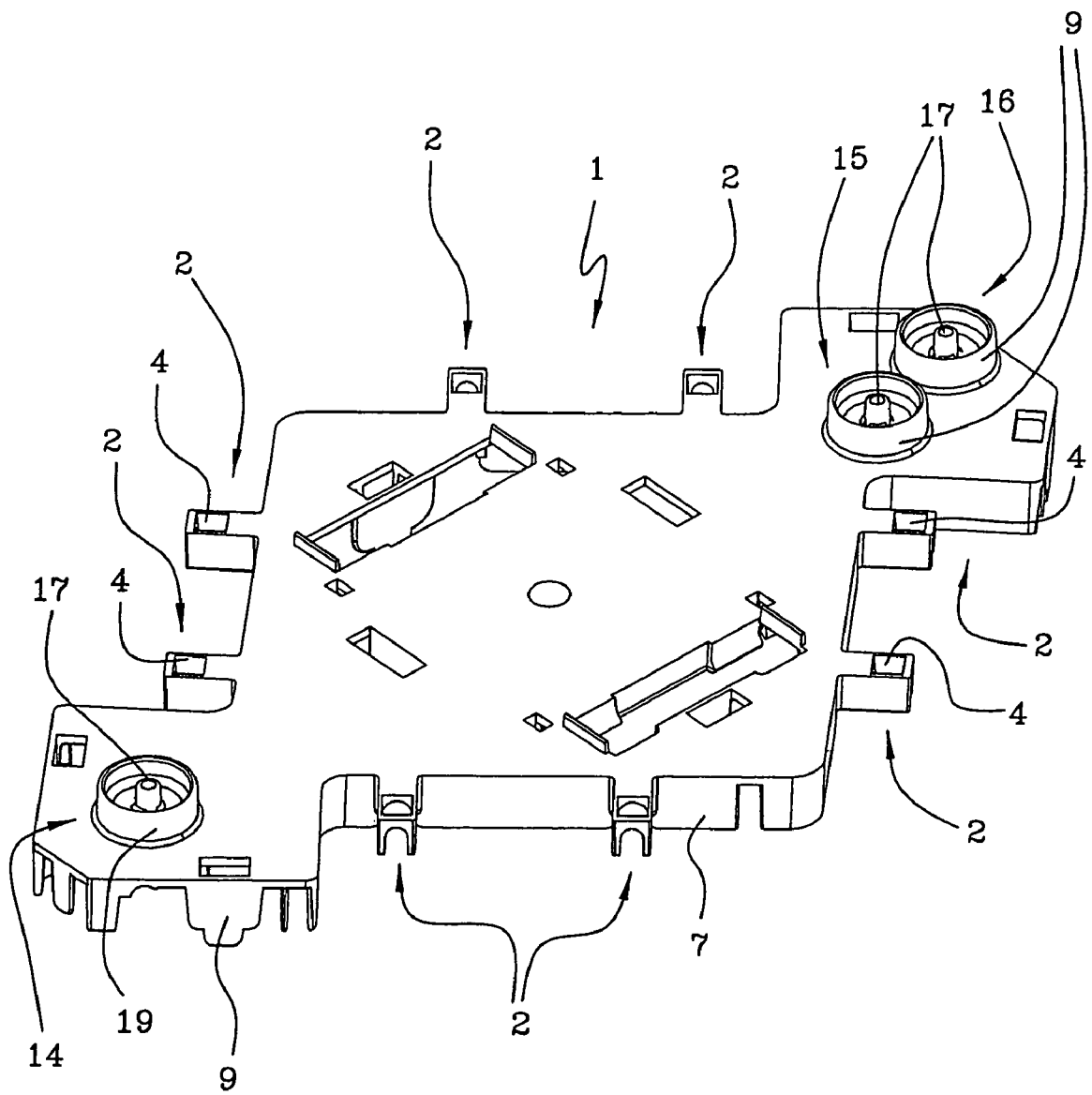
FIG. 2 is a perspective view of the external face of the base body of FIG. 1.
Figure 3:
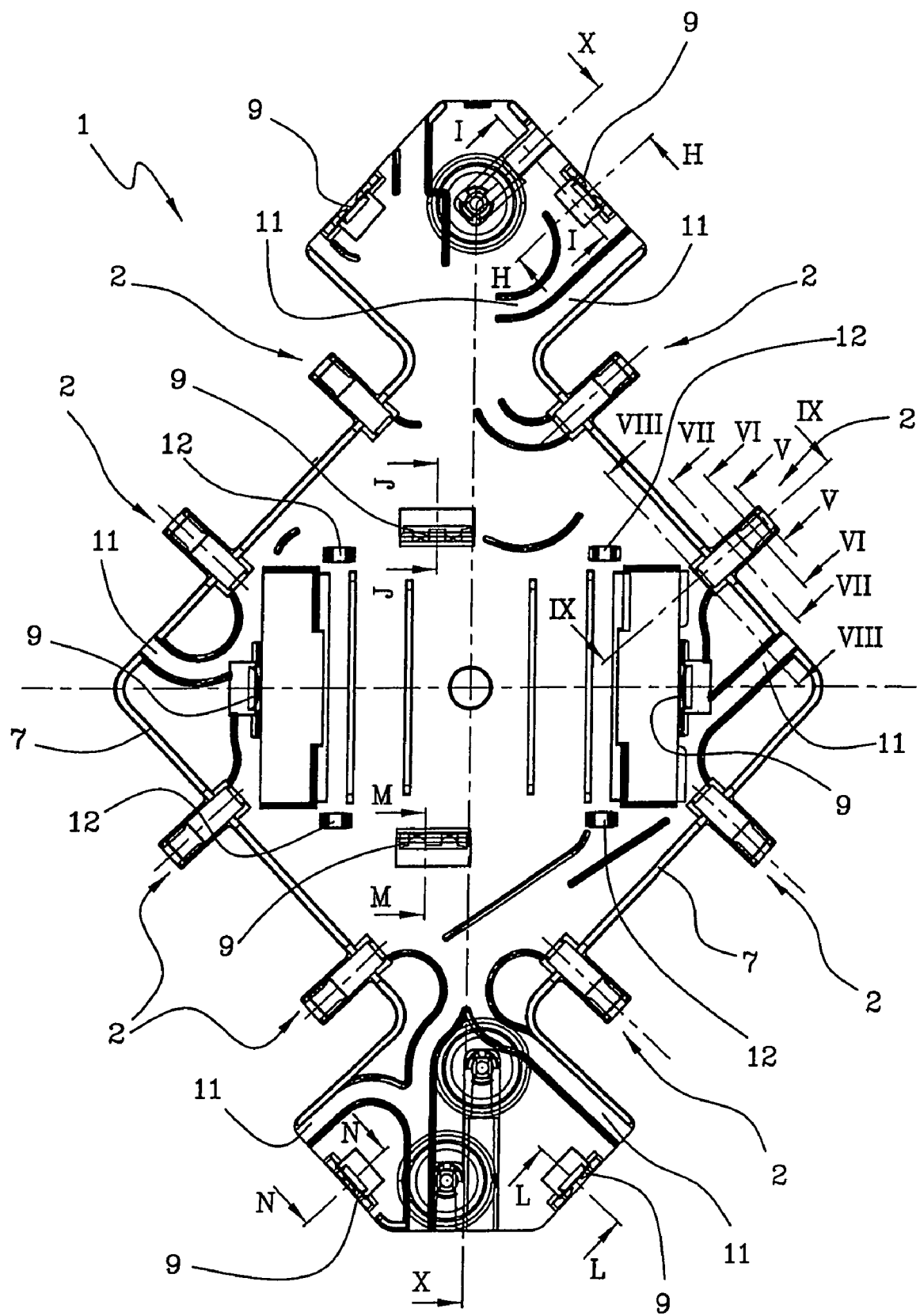
FIG. 3 is a plan view of the internal face of FIG. 1.
Figure 4:
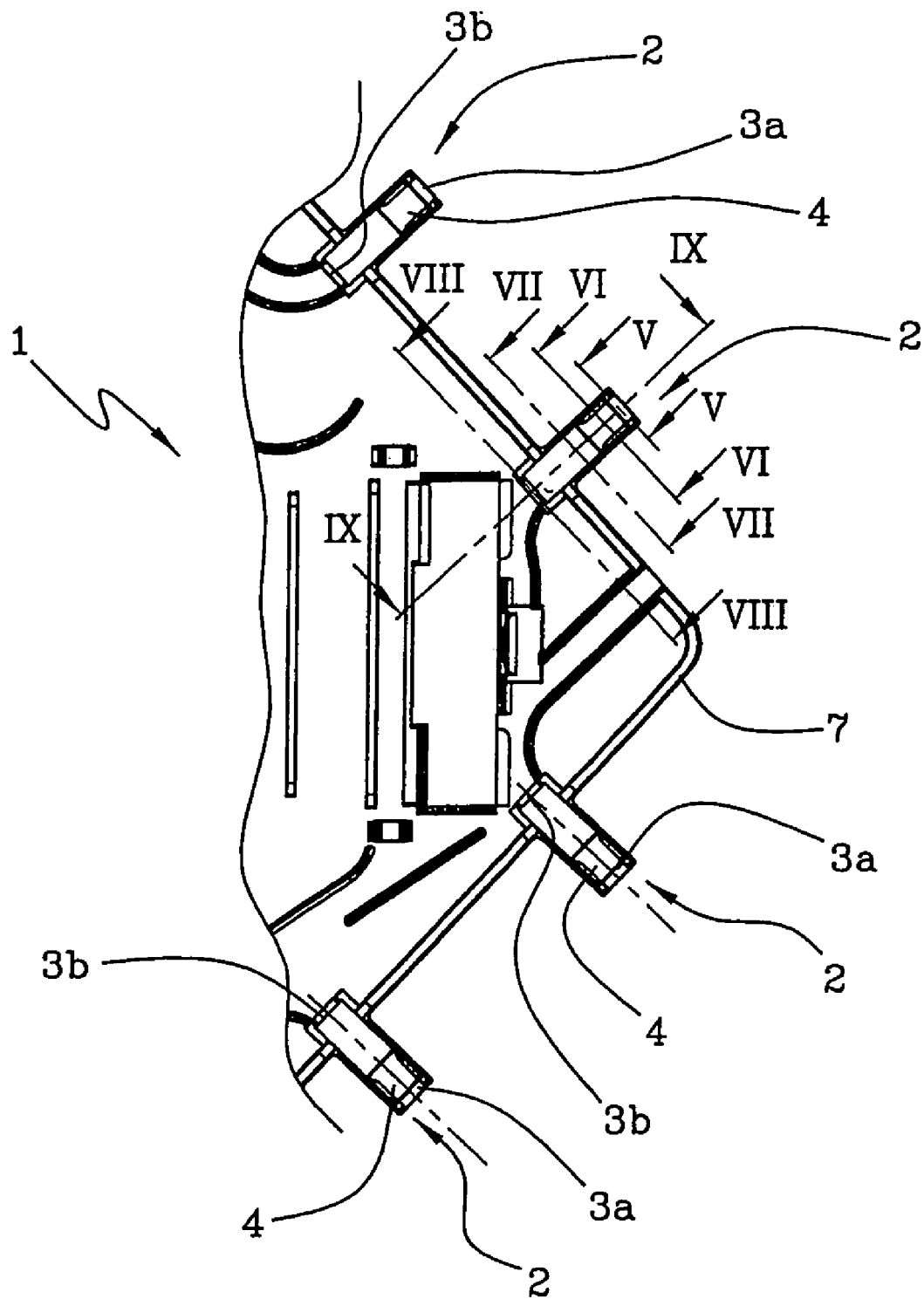
FIG. 4 is an enlarged detail of FIG. 3.
Figure 5:
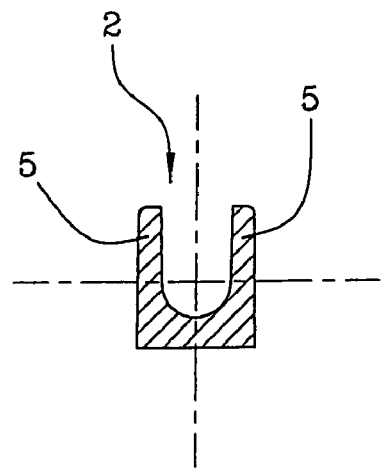
FIG. 5 is section V—V of FIG. 4.
Figure 6:
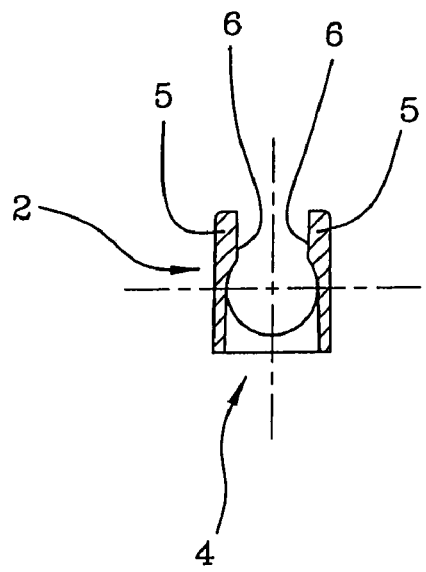
FIG. 6 is section VI—VI of FIG. 4.
Figure 7:
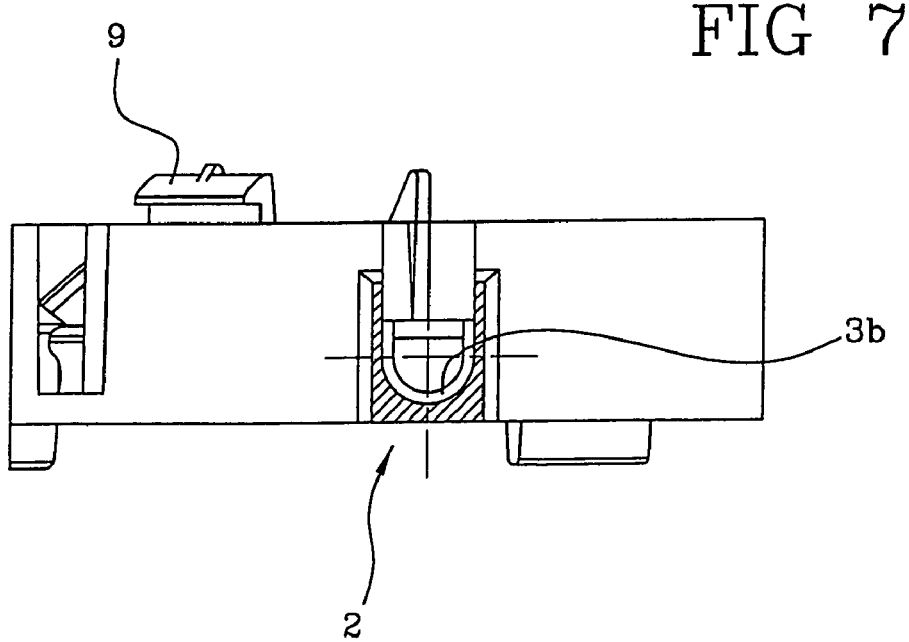
FIG. 7 is section VII—VII of FIG. 4.
Figure 8:
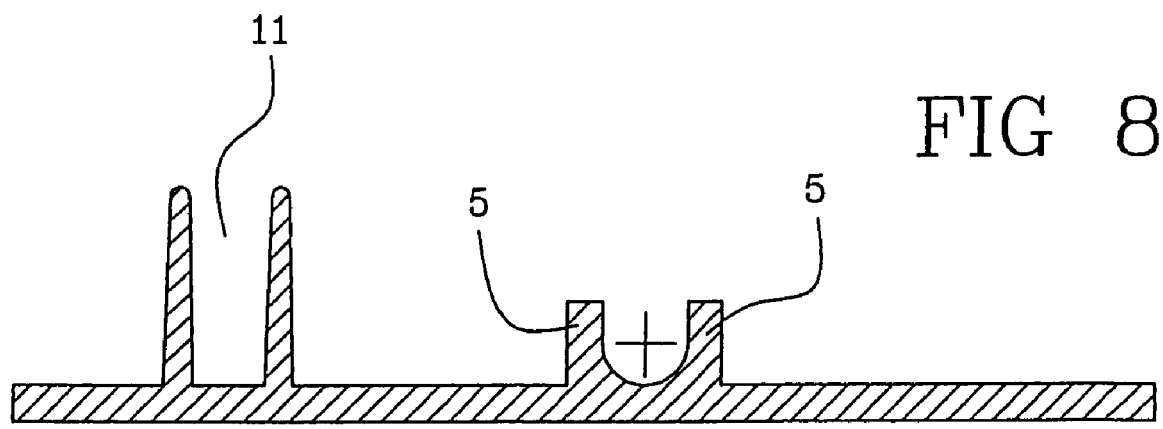
FIG. 8 is section VIII—VIII of FIG. 4.
Figure 9:
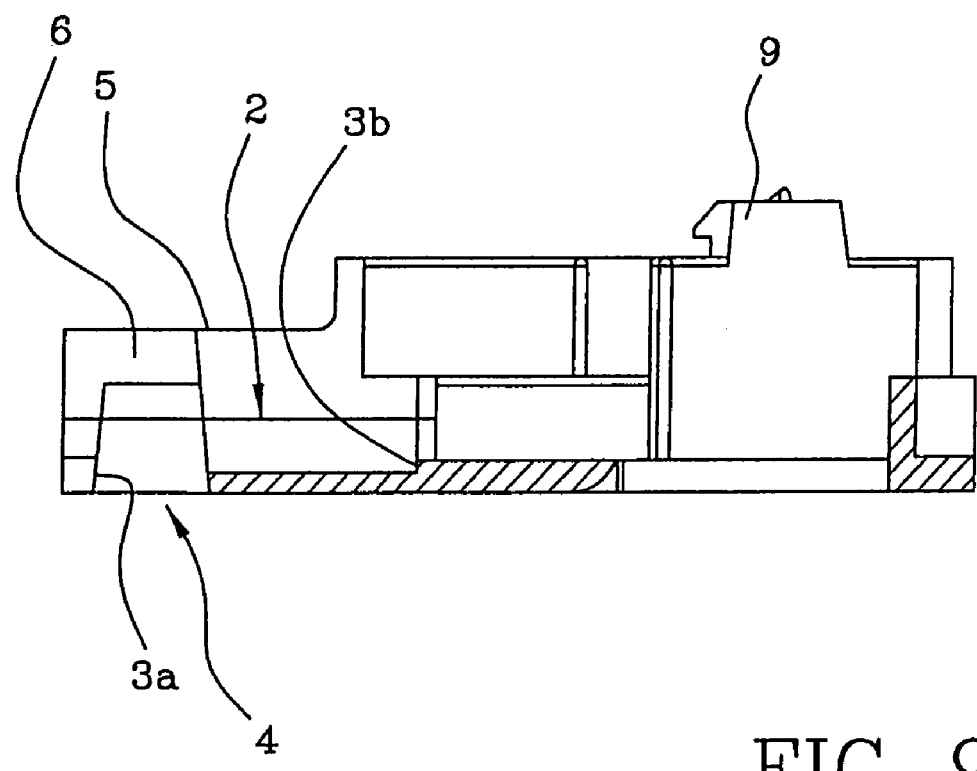
FIG. 9 is section IX—IX of FIG. 4.
Figure 10:
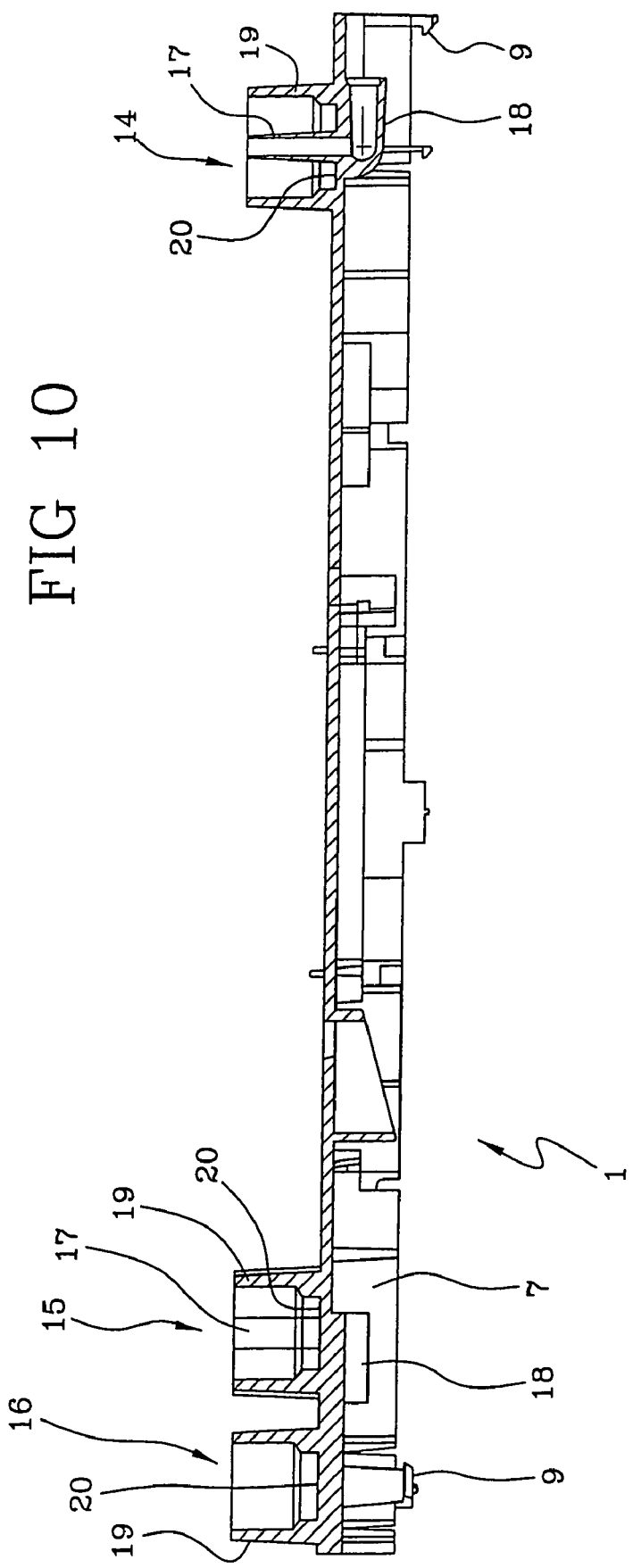
FIG. 10 is section X—X of FIG. 3.
Figure 11:
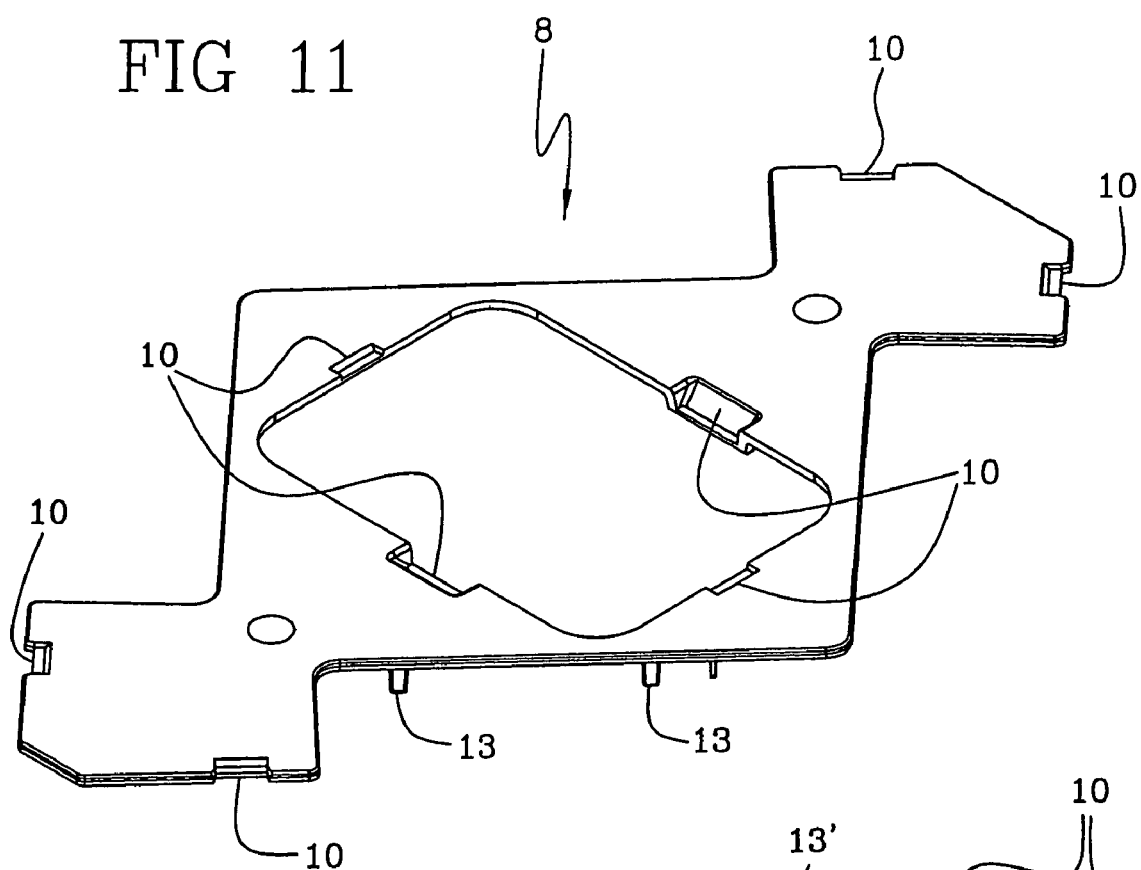
FIG. 11 is a perspective view of the upper face of the cover of the support element.
Figure 12:
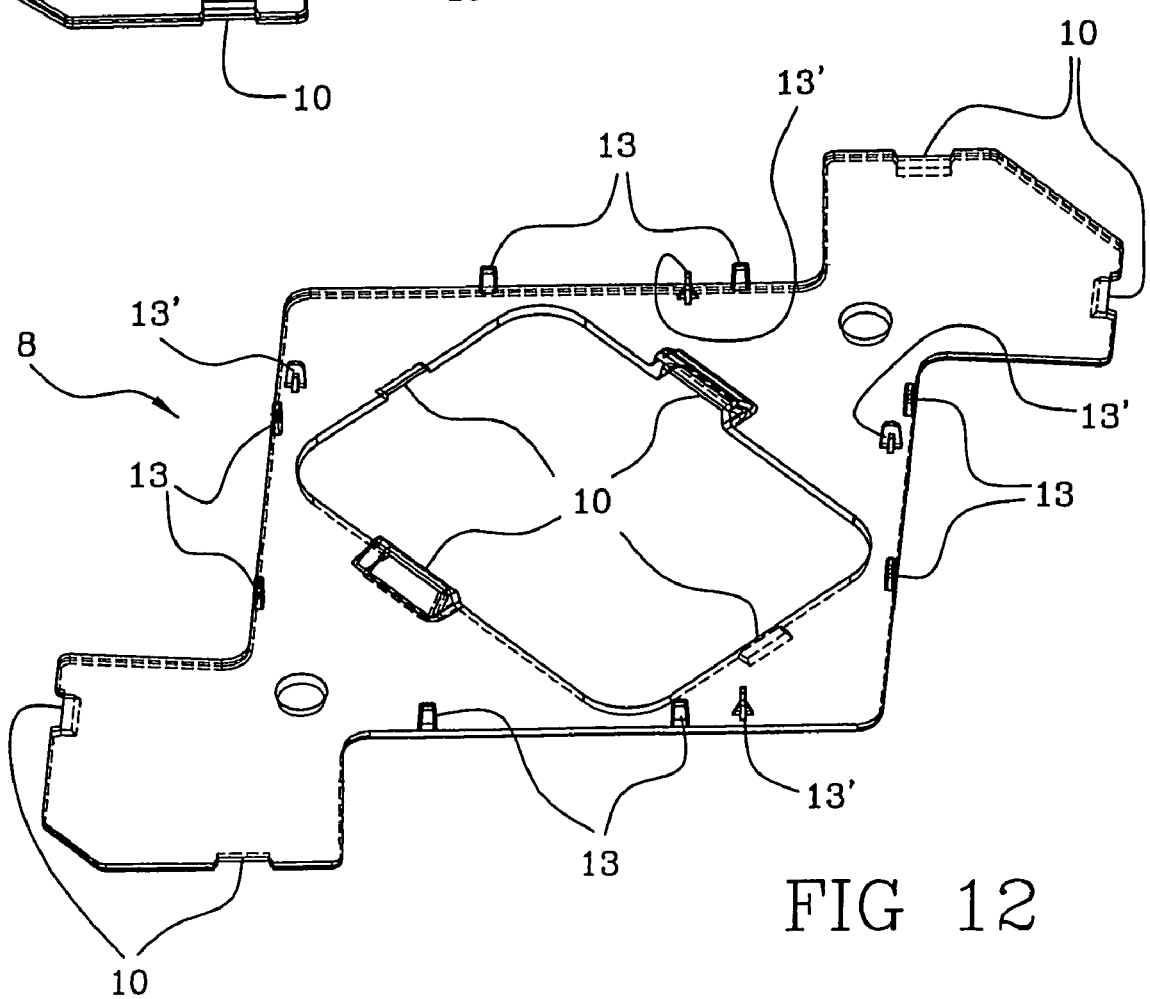
FIG. 12 is a perspective view of the lower face of the cover of FIG. 11.

The substitution fluid infeed line 33 receives an infusion or substitution fluid from a source (for example a tank or bag) and feeds it through a Y connection to a blood circulation line; or to the blood withdrawal line 31 (pre-infusion upstream of the blood treatment device 37, as in the example of FIG. 8) or to the blood return line 32 (post-infusion downstream of the blood treatment device 37, as in the example of FIG. 19).

The anticoagulant supply line 36 infeeds an anticoagulant into the blood withdrawal line 31 through a Y connection.

The blood withdrawal line 31, the substitution fluid infeed line 33, the treatment fluid infeed line 34, the waste fluid discharge line 35, each exhibit at least two tracts 38 having a predetermined length and an increased external diameter with respect to adjacent tracts thereof. The two tracts 38 having increased external diameter are arranged on the respective line at a predetermined distance one from the other. Each axial tract 38 having an increased external diameter gives rise to two external abutments. Each axial tract 38 with increased external diameter comprised between the two abutments will be press-inserted in a corresponding fixture seating 2 arranged on the periphery of the base body 1. When the complex of distribution lines is applied to the support element, each segment of line comprised between two axial tracts 38 having an increased external diameter (the pump segment) is arranged in a U-shaped arch, and is coupled to a peristaltic pump belonging to the treatment device, which pump invokes circulation of fluid in the line. The length of the segment of line comprised between the two tracts of line 38 (pump segment) is predetermined in order to guarantee a correct coupling with the peristaltic pump.

In more detail, each axial tract of line 38 with an increased external diameter comprises a joint collar 39 which contains and coaxially joins two end parts and two adjacent tracts of line: a part of an end of a tract of line is inserted into the collar 39 up to not more than half of the length of the collar 39 itself, through an axial opening in the collar 39, while the part of end of the other tract of line is inserted into the axial hole at the other end of the collar 39. A stable joint of the collar 39 with the end parts of the tracts of line can be achieved by known means, for example by hot-welding. The inter diameter of the joint collar 39 is about the same as the external diameter of the tubes forming the distribution lines. The U-shaped segment (pump segment) comprises a tube having two opposite ends inserted in two joint collars 39 and in fluid connection with two ends of two tubes, also inserted, but on the opposite side, in the same joint collars. The material used for making the arched segments of tube is suitable for operation with the peristaltic pumps and is different to the material used for the other two tubes coupled to the joint collar 39, which undergo no interaction with the peristaltic pumps. Each joint collar 39 is made of a more rigid material that that of the tracts of line the collar 39 joins. During the assembly stage of the integrated module the collar 39 is inserted snugly into the fixture seating 2. The axial length of the joint collar 39 is about the same as the axial distance between the axial locators 3a and 3b located in the fixture seating 2. The collars 39 can be slightly longer or shorter, depending on whether the desired coupling between the collar 39 and the seating 2 is achieved by axial interference or with axial play. The external diameter of the collar 39 is about the same as or slightly smaller than the maximum width of the fixture seating 2; the diameter is also greater than the minimum width of the upper insertion opening of the fixture seating 2, so that the insertion of the joint collar 39 in the fixture seating 2 is achieved by resilient friction fitting.

As previously mentioned, the length of the segment of line comprised between two joint collars 39 (pump segment) is predefined in order to obtain, once the line is coupled to the support element, a U-shaped segment precisely positioned and shaped for interaction with the peristaltic pump.

The arrangement of the complex of distribution lines on the integrated module is described in more detail herein below.

The Integrated Module.

FIGS. 18 and 19 show two integrated modules which are different essentially because of the different configurations of the distribution lines. In more detail, in the first of the modules (FIG. 18), the substitution fluid infeed line 33 is inserted into the blood withdrawal line 31 (pre-infusion), while in the second module (FIG. 19) the substitution fluid infeed line 33 (the same numbers are used in the two figures for the sake of simplicity) is inserted into the blood return line 32 (post-infusion).

The Extracorporeal Blood Treatment Apparatus.

The extracorporeal blood treatment apparatus, illustrated in FIG. 17 and indicated in its entirety by 51, comprises a housing zone 52 predisposed for receiving the integrated module for extracorporeal blood treatment (selectively one of the two above-described modules); the four peristaltic pumps 53 are located by the side of the housing zone 52 and are operatively associated to the four U-shaped segments of the fluid distribution lines in the integrated module. The apparatus can be used to perform treatments requiring the use of fewer than four pumps, in cooperation with appropriate modules provided with fewer than four U-shaped segments. The apparatus 51 further comprises a central treatment control unit, of known type and not illustrated, which controls the various treatment procedures. No special explanation of these is necessary in the present description.

The axial locators 3a and 3b ensure the precision in position and stability of the U-shaped segment cooperating with the peristaltic pumps 53. One locator alone, either external 3a or internal 3b according to the rotation direction of the corresponding pump 53, can be provided for each fixture seating 2; the locator will operate contrastingly to the action of the pump in relation to the tract of line constrained in the fixture seating 2, which action can be drawing or thrusting according to the direction of the pump and the position of the fixture seating 2 (if the seating 2 is located upstream of the pump the tube housed in the seating is drawn by the pump, while if the seating 2 is located downstream of the pump the tube is thrust). Both locators 3a and 3b can be provided in one alone of the two fixture seatings 2 located at the ends of a U-shaped segment (pump segment); and one locator 3a, 3b alone can be provided in one alone of the two fixture seatings 2 located at an end of a U-shaped segment.

The lateral reliefs 6, which define a narrow-section upper inlet of the fixture seating, are also undercuts which hold the tract of line engaged in the fixture seating 2 in position.

Integrated Module Assembly.

The assembly of the integrated module for fluid treatment comprises the following stages:

manufacture of the support element, for example by press-forming the plastic material of the two pieces which make up the element: the base body 1 and the cover 8;

fixing the blood treatment device to the support element, in particular to the external face of the base body 1;

associating the complex of distribution lines for the fluids to the support element and to the treatment device.

Fitting the treatment device to the support element includes the following stages:

Selecting a pair of connectors from connectors 14, 15 and 16, to which the seatings on the treatment device are to be fixed;

Depositing a predetermined quantity of glue on the annular seatings of each selected connector;

At least partially inserting each seating in the respective annular seating in order to achieve a mechanical lock and a liquid-sealed coupling; during the insertion stage, at least a portion of the predetermined quantity of glue enters the second zone of the annular seating, i.e. the upper broadened zone which is radially larger than the bottom zone of the annular seating; on conclusion of the insertion stage, the volume of the glue added to the volume of the portion of seating housed in the annular seating is lower than the overall volume of the annular seating, in order to avoid any glue exiting from the seating and occupying even minimally the fluid passage zone.

The coupling of the complex of fluid distribution lines to the support element comprises an insertion stage of the junction collars 39 internally of the fixture seatings 2. This stage is performed by a simple pressure fit, taking care to make sure the abutments formed by each junction collar 39 meet with the locators 3a and 3b of the respective fixture seating 2. The junction collar 39 is friction-fitted in the fixture seating 2 through the upper opening defined between the lateral walls 5, which opening is narrower than the diameter of the junction collar 39. The junction collar 39, which externally identifies the axial tract of line engaged in the fixture seating 2, is thus stably joint-coupled in the seating 2, with no need for glues and with considerable precision of positioning thanks to the coupling between the locators 3a and 3b and the ends of the junction collar 39.

The cover 8 is coupled to the base body 1 after the distribution lines have been engaged. The cover 8 at least partially closes off the lines engaged to the base body 1 and guarantees the lines' housed stability.

The integrated module is destined to be replaced by a new module. The support element can be easily separated from the distribution lines and the treatment device and re-used, after suitable washing and sterilizing procedures, as a support element for a new treatment module; or it can be disposed of suitably.

Detaching the distribution lines is done by removing the cover 8 and extracting the complex of lines from the housing zone on the base body 1: the extraction procedure is made easier by the through-holes 4 which enable an extracting pressure to be exerted from the bottom on the collars 39, causing the lines to exit through the upper openings of the fixture seatings 2.

The invention claimed is:

1. A support element for an integrated module for extracorporeal blood treatment, comprising:
   a base body:
   at least one fixture seating located on the base body, said at least one fixture seating being axially extended and configured to house an axially extended tract of a fluid distribution line;
   an axial locator arranged in said seating fixture, said axial locator being configured to position said axially extended tract of a fluid distribution line in a fixed position, said axial locator being further configured to interact with a corresponding element predisposed on said axially extended tract of a fluid distribution line, said at least one axial locator having an undercut surface, said undercut surface being positioned in an axial direction of the axially extended tract of a fluid distribution line.

2. The support element of claim 1, wherein said axial locator is a first axial locator, said support element further comprising a second axial locator, said first and second axial locators being axially reciprocally separated, wherein the axially extended tract of a fluid distribution line is positioned in a fixed position between the first and second axial locators.

3. The support element of claim 1, wherein the at least one fixture seating comprises a superiorly-open channel, said channel being configured to accept the axially extended tract of a fluid distribution line said axial locator having an edge projecting into the channel from a wall delimiting the channel.

4. The support element of claim 1, further comprising at least one pair of fixture seatings, said at least one pair having first and second fixture seatings being configured on a periphery of the base body, said at least one pair of fixture seatings being further configured to receive first and second ends of a U-shaped segment of at least one fluid distribution line, the U-shaped segment being configured to cooperate with a peristaltic pump.

5. The support element of claim 4, wherein the U-shaped segment projects outside the periphery of the base body.

6. The support element of claim 4, wherein the base body further comprises:
- a flat plate-shaped part having a plurality of perimeter sides, said plurality of perimeter sides defining a polygonal shape of the base body;
- a plurality of pairs of fixture seatings, each pair of fixture seatings including first and second fixture seatings, said first and second fixture seatings being provided on one of the plurality of perimeter sides, wherein said first and second fixture seatings being arranged adjacent and reciprocally parallel to one another.

7. The support element of claim 1, wherein the base body has at least one flat sheet-shaped part, said at least one flat sheet-shaped part having an internal face and an external face, said internal face having a raised, edge on a perimeter of the internal face, the support element further comprising:
- a cover coupled to the base body, said cover being configured to cover at least a part of the internal face of the base body and having at least one flat plate-shaped part, said cover also having a cover perimeter corresponding to a perimeter of the internal face of the base body;
- a containment space positioned between the internal face of the base body and an internal face of the cover, said containment space being configured to house a complex of fluid distribution lines; and
- a connector positioned on the internal face of the base body configured to engage and constrain the complex of fluid distribution lines;
- said raised edge on the perimeter of the internal face of the base body being configured to laterally delimit said containment space, said base body further comprising at least one hooking tab including a single piece and the base body, said hooking tab being configured to removably couple the cover to the base body.

8. The support element of claim 1, wherein the base body has at least one flat sheet-shaped part, said at least one flat sheet-shaped part having an internal face and an external face, the support element further comprising:
- a cover coupled to the base body, configured to cover at least a part of the internal face of the base body, said cover having at least one flat plate-shaped part;
- a containment space delimited by the internal face of the base body and an internal face of the cover, said containment space being configured to house a complex of fluid distribution lines; and
- at least one guide channel positioned on the internal face of the base body, said at least one guide channel being configured to receive at least a first axial tract of a fluid distribution line and further configured to define a guided pathway for the first axially extended tract of the fluid distribution line, a height of the at least one guide channel being at least twice a width of the at least one guide channel, said at least one guide channel being configured to house and laterally contain at least first and second axial tracts of line, one of the first and second axial tracts of line being superposed on the other;
- wherein the at least one guide channel is delimited by first and second lateral walls, said first and second lateral walls rising from the internal face of the base body.

9. A support element for an integrated module for extracorporeal blood treatment, comprising:
- a base body:
- at least one fixture seating located on the base body, said at least one fixture seating being axially extended and configured to house an axially extended tract of a fluid distribution line, said at least one fixture seating being configured to accept a forced insertion and a resilient joint-coupling of the axially extended tract of a fluid distribution line, the at least one fixture seating having at least one opening configured to accept insertion of the axially extended tract of a fluid distribution line, the at least one opening having a passage section with a width, at least a portion of said width being smaller than a maximum width of the at least one fixture seating;
- an axial locator arranged in said seating fixture, said axial locator being configured to position said axially extended tract of a fluid distribution line in a fixed position, said axial locator being further configured to interact with a corresponding element predisposed on said axially extended tract of a fluid distribution line.

10. The support element of claim 9, wherein said axial locator is a first axial locator, said support element further comprising a second axial locator, said first and second axial locators being axially reciprocally separated, wherein the axially extended tract of a fluid distribution line is positioned in a fixed position between the first and second axial locators.

11. The support element of claim 9, wherein the at least one fixture seating comprises a superiorly-open channel, said channel being configured to accept the axially extended tract of a fluid distribution line said axial locator having an edge projecting into the channel from a wall delimiting the channel.

12. The support element of claim 9, further comprising at least one pair of fixture seatings, said at least one pair having first and second fixture seatings being configured on a periphery of the base body, said at least one pair of fixture seatings being further configured to receive first and second ends of a U-shaped segment of at least one fluid distribution line, the U-shaped segment being configured to cooperate with a peristaltic pump.

13. The support element of claim 12, wherein the U-shaped segment projects outside the periphery of the base body.

14. The support element of claim 12, wherein the base body further comprises:
- a flat plate-shaped part having a plurality of perimeter sides, said plurality of perimeter sides defining a polygonal shape of the base body;
- a plurality of pairs of fixture seatings, each pair of fixture seatings including first and second fixture seatings, said first and second fixture seatings being provided on one of the plurality of perimeter sides, wherein said first and second fixture seatings being arranged adjacent and reciprocally parallel to one another.

15. The support element of claim 9, wherein the base body has at least one flat sheet-shaped part, said at least one flat sheet-shaped part having an internal face and an external face, said internal face having a raised edge on a perimeter of the internal face, the support element further comprising:
- a cover coupled to the base body, said cover being configured to cover at least a part of the internal face of the base body and having at least one flat plate-shaped part, said cover also having a cover perimeter corresponding to a perimeter of the internal face of the base body;
- a containment space positioned between the internal face of the base body and an internal face of the cover, said containment space being configured to house a complex of fluid distribution lines; and
- a connector positioned on the internal face of the base body configured to engage and constrain the complex of fluid distribution lines;
- said raised edge on the perimeter of the internal face of the base body being configured to laterally delimit said containment space, said base body further comprising at least one hooking tab including a single piece and the base body, said hooking tab being configured to removably couple the cover to the base body.

16. The support element of claim 9, wherein the base body has at least one flat sheet-shaped part, said at least one flat sheet-shaped part having an internal face and an external face, the support element further comprising:
- a cover coupled to the base body, configured to cover at least a part of the internal face of the base body, said cover having at least one flat plate-shaped part;
- a containment space delimited by the internal face of the base body and an internal face of the cover, said containment space being configured to house a complex of fluid distribution lines; and
- at least one guide channel positioned on the internal face of the base body, said at least one guide channel being configured to receive at least a first axial tract of a fluid distribution line and further configured to define a guided pathway for the first axially extended tract of the fluid distribution line, a height of the at least one guide channel being at least twice a width of the at least one guide channel, said at least one guide channel being configured to house and laterally contain at least first and second axial tracts of line, one of the first and second axial tracts of line being superposed on the other;
- wherein the at least one guide channel is delimited by first and second lateral walls, said first and second lateral walls rising from the internal face of the base body.

17. A support element for an integrated module for extracorporeal blood treatment, comprising:
- a base body;
- at least one fixture seating located on the base body, said at least one fixture seating being axially extended and configured to house an axially extended tract of a fluid distribution line, said at least one fixture seating further having a primary surface for receiving the axially extended tract of the fluid distribution line, said surface having at least two undercut surfaces, said at least two undercut surfaces being configured to obstruct at least a first and second displacement of the axially extended tract of the fluid distribution line, said first displacement being in an axial direction and said second displacement being in an upwards extraction direction passing through an upper insertion opening;
- an axial locator arranged in said seating fixture, said axial locator being configured to position said axially extended tract of a fluid distribution line in a fixed position, said axial locator being further configured to interact with a corresponding element predisposed on said axially extended tract of a fluid distribution line.

18. The support element of claim 17, wherein said axial locator is a first axial locator, said support element further comprising a second axial locator, said first and second axial locators being axially reciprocally separated, wherein the axially extended tract of a fluid distribution line is positioned in a fixed position between the first and second axial locators.

19. The support element of claim 17, wherein the at least one fixture seating comprises a superiorly-open channel, said channel being configured to accept the axially extended tract of a fluid distribution line said axial locator having an edge projecting into the channel from a wall delimiting the channel.

20. The support element of claim 17, further comprising at least one pair of fixture seatings, said at least one pair having first and second fixture seatings being configured on a periphery of the base body, said at least one pair of fixture seatings being further configured to receive first and second ends of a U-shaped segment of at least one fluid distribution line, the U-shaped segment being configured to cooperate with a peristaltic pump.

21. The support element of claim 20, wherein the U-shaped segment projects outside the periphery of the base body.

22. The support element of claim 20, wherein the base body further comprises:
- a flat plate-shaped part having a plurality of perimeter sides, said plurality of perimeter sides defining a polygonal shape of the base body;
- a plurality of pairs of fixture seatings, each pair of fixture seatings including first and second fixture seatings, said first and second fixture seatings being provided on one of the plurality of perimeter sides, wherein said first and second fixture seatings being arranged adjacent and reciprocally parallel to one another.

23. A support element for an integrated module for extracorporeal blood treatment, comprising:
- a base body;
- at least one fixture seating located on the base body, said at least one fixture seating being axially extended and configured to house an axially extended tract of a fluid distribution line, said at least one fixture seating further having at least one superior opening configured to accept a forced insertion of the axially extended tract of the fluid distribution line and at least one inferior through-hole facing the at least one superior opening, said at least one inferior through-hole being configured to allow an exertion of pressure onto the axially extended tract of a fluid distribution line through said at least one inferior through-hole, said axially extended tract of a fluid distribution line engaging the at least one fixture seating, wherein said exertion enables an extraction of the axially extended tract of a fluid distribution line through the superior opening;
- an axial locator arranged in said seating fixture, said axial locator being configured to position said axially extended tract of a fluid distribution line in a fixed position, said axial locator being further configured to interact with a corresponding element predisposed on said axially extended tract of a fluid distribution line.

24. The support element of claim 23, wherein said axial locator is a first axial locator, said support element further comprising a second axial locator, said first and second axial locators being axially reciprocally separated, wherein the axially extended tract of a fluid distribution line is positioned in a fixed position between the first and second axial locators.

25. The support element of claim 23, wherein the at least one fixture seating comprises a superiorly-open channel, said channel being configured to accept the axially extended tract of a fluid distribution line said axial locator having an edge projecting into the channel from a wall delimiting the channel.

26. The support element of claim 23, further comprising at least one pair of fixture seatings, said at least one pair having first and second fixture seatings being configured on a periphery of the base body, said at least one pair of fixture seatings being further configured to receive first and second ends of a U-shaped segment of at least one fluid distribution line, the U-shaped segment being configured to cooperate with a peristaltic pump.

27. The support element of claim 26, wherein the U-shaped segment projects outside the periphery of the base body.

28. The support element of claim 26, wherein the base body further comprises:
a flat plate-shaped part having a plurality of perimeter sides, said plurality of perimeter sides defining a polygonal shape of the base body;
a plurality of pairs of fixture seatings, each pair of fixture seatings including first and second fixture seatings, said first and second fixture seatings being provided on one of the plurality of perimeter sides, wherein said first and second fixture seatings being arranged adjacent and reciprocally parallel to one another.

29. A support element for an integrated module for extracorporeal blood treatment, comprising:
a base body;
at least one fixture seating located on the base body, said at least one fixture seating being axially extended and configured to house an axially extended tract of a fluid distribution line;
an axial locator arranged in said seating fixture, said axial locator being configured to position said axially extended tract of a fluid distribution line in a fixed position, said axial locator being further configured to interact with a corresponding element predisposed on said axially extended tract of a fluid distribution line; and
a lateral relief projecting inside the channel from at least one of the first and second lateral walls, the at least one lateral relief forming at least one undercut surface positioned in an extraction direction of the axially extended tract of a fluid distribution line through the superior opening of the channel, the at least undercut surface being configured inferior to the upper edge of the lateral wall wherein;
the at least one fixture seating comprises a channel having a superior opening configured to accept an insertion of the axially extended tract of the fluid distribution line, the channel extending axially and at least partially projecting in an external direction, said channel projecting outside of a perimeter border of the base body, the channel having first and second lateral walls, said first and second lateral walls being adjacent to each other, said first lateral wall having a first upper edge and said second lateral wall having a second upper edge,
the superior opening being bounded by the first and second upper edges of the first and second lateral walls.

30. The support element of claim 29, wherein said lateral relief is a first lateral relief, said support element comprising a second lateral relief, said first and second lateral reliefs being configured to face one another and cooperate to obstruct an extraction of the axially extended tract of the fluid distribution line.

31. The support element of claim 29, wherein the channel is configured to constrain a tract of an end segment of U-shaped line, said lateral relief being provided in a part of end of the channel facing the segment of U-shaped line.

32. The support element of claim 29, wherein the at least one undercut surface is configured to enable extraction of the axially extended tract of a fluid distribution line by a forcing movement.

33. A support element for an integrated module for extracorporeal blood treatment, comprising:
a base body;
at least one fixture seating located on the base body, said at least one fixture seating being axially extended and configured to house an axially extended tract of a fluid distribution line;
an axial locator arranged in said seating fixture, said axial locator being configured to position said axially extended tract of a fluid distribution line in a fixed position, said axial locator being further configured to interact with a corresponding element predisposed on said axially extended tract of a fluid distribution line;
a complex of distribution lines;
a cover removably couplable to the base body, said cover being configured to cover at least a part of the internal face of the base body;
a containment space between the internal face of the base body; and
an internal face of the cover, said containment space being configured to house at least a part of the complex of distribution lines, wherein the base body is flat-plate shaped and the at least one fixture seating extends over an internal face of the base body.

34. The support element of claim 33, wherein the cover exhibits at least one tooth projecting downwards, said tooth entering at least partially into the at least one fixture seating, said tooth further limiting a raising movement of the axial tract line constrained in the at least one fixture seating.

35. The support element of claim 33, wherein the internal face of the base body comprises a raised edge on a perimeter of the internal face of the base body, said raised edge being configured to laterally contain at least a part of the complex of distribution lines, the cover of the support element having a flat plate-shape and covering a perimeter substantially similar to the perimeter of the internal face of the base body.

36. The support element of claim 35, wherein the base body comprises at least one hooking tab formed of a single piece along with the base body, said hooking tab being configured to removably couple the cover to the base body.

37. The support element of claim 33, wherein the at least one fixture seating comprises an axial end tract extending axially and internally to a perimeter side of the base body and an end tract extending axially and external to the perimeter side of the base body.

38. A support element for an integrated module for extracorporeal blood treatment, comprising:
a base body;
at least one fixture seating configured on the base body to receive and constrain an axially extending tract of a fluid distribution line, the at least one fixture seating having a channel with an opening configured to accept a forced insertion of the axially extended tract of the fluid distribution line, the channel being axially extended and at least partially projecting axially outside a perimeter edge of the base body, at least the part of the channel projecting axially outside a perimeter edge of the base body being laterally delimited by first and second walls, the first and second walls being adjacent to each other, each of said first and second walls having an upper edge delimiting the opening configured to accept a forced insertion; and at least one lateral relief projecting into the channel from at least one of the first and second walls, the at least one lateral relief forming at least one undercut surface positioned in an extraction direction of the axially extended tract of the fluid distribution line through the superior opening of the channel, the at least one undercut surface being arranged inferior to a superior edge of at least one of the first and second walls.

39. A support element for an integrated module for extracorporeal blood treatment, comprising:

a base body;

at least one fixture seating located on the base body, said at least one fixture seating being axially extended and configured to house an axially extended tract of a fluid distribution line;

an axial locator arranged in said seating fixture, said axial locator being configured to position said axially extended tract of a fluid distribution line in a fixed position, said axial locator being further configured to interact with a corresponding element predisposed on said axially extended tract of a fluid distribution line;

at least first, second, and third connectors being joined to the base body and separated from each other by a distance, said at least first, second, and third connectors being further configured to receive and constrain corresponding seatings of a blood treatment device, said blood treatment device being mountable on the support element, each of said first, second, and third connectors defining a fluid passage having a first terminal portion configured to be placed in fluid communication with a corresponding channel, said channel being present in a respective seating included in the blood treatment device, and a second terminal portion configured to be placed in fluid communication with a fluid distribution line being coupled to the base body.

40. The support element of claim 39, wherein the first and the second connectors are formed of a single piece along with the base body.

41. The support element of claim 39, wherein said third connector is formed of a single piece along with the base body, said first, second, and third connectors being configured in pairs, each pair having a different interaxes from another pair, the interaxes corresponding with interaxes of pairs of seatings associated with various blood treatment devices, said various blood treatment devices being mountable on the support element.

42. The support element of claim 39, wherein each of the first, second, and third connectors comprises:

a tubular channel, defining the first terminal portion;

a sealing collar, provided in a position radially external to the tubular channel; and a continuous connecting wall provided between a lateral external surface of the tubular channel and a lateral internal surface of the sealing collar, said continuous connecting wall defining an annular seating for each at least one fixture seating.

43. The support element of claim 39, wherein the tubular channel defines the first terminal position, said tubular channel being arranged coaxial to the sealing collar, the annular seating having a bottom delimited by the connecting wall.

44. The support element of claim 42, wherein the annular seating has a radius, said radius increasing in a distal direction from the bottom of the annular seating.

45. The support element of claim 44, wherein the annular seating comprises:

a first zone having a constant radius, said first zone being adjacent to the bottom of the annular seating;

a second zone having a constant radius larger than the constant radius of the first zone; and a transitional third zone positioned between the first zone and the second zone, said transitional third zone having a radius progressively increasing in a distal direction from the bottom of the annular seating.

46. The support element of claim 42, wherein the tubular channel and the sealing collar of each of the first, second, and third connectors are parallel to each other, said tubular channels and sealing collars emerging from the base body and defining a single coupling direction with the corresponding seatings of a blood treatment device.

47. The support element of claim 42, wherein the first, second, and third connectors and the base body are made of a rigid material, said material providing mechanical support to the blood treatment device.

48. The support element of claim 42, wherein the first, second, and third connectors are not aligned with each other.

49. The support element of claim 42, wherein the first, second, and third connectors are directly constrained to the base body.

50. The support element of claim 42, wherein the first, second, and third connectors are each provided on a first face of the base body, said first face being opposite a second face of the base body, said base body bearing the at least one fixture seating.

51. A fluid distribution line for an integrated module for an extracorporeal blood treatment, comprising:

a first tract of line having a larger external diameter than adjacent tracts of line; and first and second external abutments, the first tract of line is positioned between the first and second external abutments, said first tract of line being configured for insertion in the fixture seating configured on a support element comprising:

a base body;

at least one fixture seating located on the base body said at least one fixture seating being axially extended and configured to house an axially extended tract of a fluid distribution line; and an axial locator arranged in said seating fixture, said axial locator being configured to position said axially extended tract of a fluid distribution line in a fixed position, said axial locator being further configured to interact with a corresponding element predisposed on said axially extended tract of a fluid distribution line.

52. The distribution line of claim 51, comprising:

a second tract of line, said first and second tracts of line being separated axially from each other; and a segment of line being positioned between the first and second tracts of line, said segment of line being configured to form a U-shaped arched segment, said U-shaped arched segment being coupled to a peristaltic pump.

53. The distribution line of claim 51, wherein the first tract of line comprises a junction collar, said junction collar accepting and joining first and second end zones of first and second parts of a fluid-connected line.

54. The distribution line of claim 53, wherein the junction collar is formed of a rigid material, said rigid material being more rigid than a material forming the first and second end zones of the first and second parts of fluid-connected line connected by the junction collar.

55. A series of elements configured to be coupled to each other, comprising:
a first element, said first element being the a support element comprising:
a base body;
at least one fixture seating located on the base body, said at least one fixture seating being axially extended and configured to house an axially extended tract of a fluid distribution line; and
an axial locator arranged in said seating fixture, said axial locator being configured to position said axially extended tract of a fluid distribution line in a fixed position, said axial locator being further configured to interact with a corresponding element predisposed on said axially extended tract of a fluid distribution line;
a second element, said second element being a complex of fluid distribution lines, said fluid distribution lines comprising at least one tract of line; and
first and second external abutments, the at least one tract of line being positioned between the first and second external abutments, said at least one tract of line being configured for insertion in the fixture seating configured on the support element.

56. An assembly process of the series of elements of claim 55, wherein the at least one tract of line having a larger external diameter being positioned between the first and second external abutments is inserted in the at least one fixture seating provided on the support element, the first and second abutments overlapping with the axial locator configured in the at least one fixture seating, the support element being provided with a cover, said cover being subsequently coupled to the base body to at least partially cover the at least one tract of line having a larger diameter.

57. An integrated module for extracorporeal blood treatment, comprising:
a support element comprising:
a base body;
at least one fixture seating located on the base body, said at least one fixture seating being axially extended and configured to house an axially extended tract of a fluid distribution line; and
an axial locator arranged in said seating fixture, said axial locator being configured to position said axially extended tract of a fluid distribution line in a fixed position, said axial locator being further configured to interact with a corresponding element predisposed on said axially extended tract of a fluid distribution line;
at least one blood treatment device mounted on the support element, said at least one blood treatment device comprising at least first and second chambers, said first and second chambers being separated by at least one semi-permeable membrane;
a complex of fluid distribution lines associated to the support element and cooperating with the blood treatment device, said complex of fluid distribution lines comprising at least one line having a larger external diameter than adjacent tracts of line;
first and second external abutments, wherein the at least one tract of line with a larger external diameter is positioned between the first and second external abutments, said at least one tract of line with a larger external diameter being configured for insertion in the fixture seating provided on the support element.

58. The integrated module of claim 57, for use in treatment of renal insufficiency, wherein the blood treatment device is selected from a group comprising hemofiltration, hemodialysis, high-flow filtration, and hemodiafiltration devices.

59. An apparatus for extracorporeal treatment of blood, comprising:
a housing zone for receiving an integrated module for extracorporeal blood treatment according to claim 57; and
one or more pumps configured to circulate fluid and cooperate with the complex of fluid distribution lines of the integrated module.

60. An integrated module for extracorporeal blood treatment, having:
a support element comprising:
a base body;
at least one fixture seating located on the base body, said at least one fixture seating being axially extended and configured to house an axially extended tract of a fluid distribution line; and
an axial locator arranged in said seating fixture, said axial locator being configured to position said axially extended tract of a fluid distribution line in a fixed position, said axial locator being further configured to interact with a corresponding element predisposed on said axially extended tract of a fluid distribution line;
at least one blood treatment device mounted on the support element, said at least one blood treatment device comprising at least first and second chambers, said first and second chambers being separated by at least one semi-permeable membrane; and
a complex of fluid distribution lines associated to the support element and cooperating with the blood treatment device, said blood treatment device further comprising:
a containment body housing said first and second chambers being separated by said at least one semi-permeable membrane;
first and second counter-connectors associated to the containment body, said first and second counter-connectors being fixed to first, second, or third connectors associated with the base body, the first and second connectors being set in fluid connection with the second chamber of the blood treatment device and first terminal portions of the first and second connectors;
at least one inlet port to the first chamber; and
at least one outlet port from the first chamber, said blood treatment device being fixed to said base body by at least one pair of connectors from the group comprising said first, second, and third connectors.

61. The module of claim 60, wherein the complex of fluid distribution lines further comprises at least one discharge line of waste fluid, said at least one discharge line being set in communication with the second terminal portion of one of the first, second, and third connectors.

62. The module of claim 61, wherein the complex of fluid distribution lines further comprises at least one infeed line of a treatment fluid, said at least one infeed line being in communication with the second terminal portion of another of the first, second, and third connectors.

63. The module of claim 61, wherein at least one of the lines is attached to the support element, said at least one line defining at least one U-shaped arched segment on the support element and said at least one line being further configured to cooperate with a peristaltic pump.

64. The module of claim 63, wherein the U-shaped segment extends outside of the perimeter wall of the support element.

65. The module of claim 60, wherein the complex of fluid distribution lines further comprises: at least one blood withdrawal line, said at least one blood withdrawal line being in communication with the inlet port of the first chamber, and at least one blood return line, said at least one blood return line being in communication with the outlet port of the first chamber.

66. The integrated module of claim 60, for use in treatment of renal insufficiency, wherein the blood treatment device is selected from a group comprising hemofiltration, hemodialysis, high-flow filtration, and hemodiafiltration devices.

67. An apparatus for extracorporeal treatment of blood, comprising:

a housing zone for receiving an integrated module for extracorporeal blood treatment according to claim 60; and one or more pumps configured to circulate fluid and cooperate with the complex of fluid distribution lines of the integrated module.

* * * * *

UNITED STATES PATENT AND TRADEMARK OFFICE
CERTIFICATE OF CORRECTION

PATENT NO. : 7,232,418 B2  Page 1 of 1
APPLICATION NO. : 10/771415
DATED : June 19, 2007
INVENTOR(S) : Neri et al.

It is certified that error appears in the above-identified patent and that said Letters Patent is hereby corrected as shown below:

Column 12, line 40, "body:" should read --body;--.

Column 13, line 26, "raised, edge" should read --raised edge--.

Column 14, line 9, "body:" should read --body;--.

Column 17, line 53, "wherein;" should read --wherein:--.

Column 20, line 48, "body said" should read --body, said--.

Column 21, line 10, "being the a" should read --being a--.

Signed and Sealed this

Fourteenth Day of August, 2007

JON W. DUDAS
*Director of the United States Patent and Trademark Office*